(12) United States Patent
Gambale et al.

(10) Patent No.: US 6,802,858 B2
(45) Date of Patent: Oct. 12, 2004

(54) VASCULAR INDUCING IMPLANTS

(75) Inventors: Richard A. Gambale, Tyngsboro, MA (US); Stephen J. Forcucci, Medford, MA (US); Michael F. Weiser, Groton, MA (US); Richard T. Choh, Waltham, MA (US); Sean Forde, Watertown, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/774,320

(22) Filed: Jan. 31, 2001

(65) Prior Publication Data

US 2001/0004683 A1 Jun. 21, 2001

Related U.S. Application Data

(63) Continuation of application No. 09/164,173, filed on Sep. 30, 1998, now Pat. No. 6,458,092.

(51) Int. Cl.[7] .................................................. A61F 2/06
(52) U.S. Cl. ..................................... 623/1.35; 623/1.15
(58) Field of Search ............................... 623/1.35, 1.36, 623/1.15, 1.16, 1.2, 1.21, 1.22; 267/166, 167, 168, 180

(56) References Cited

U.S. PATENT DOCUMENTS

| | | | |
|---|---|---|---|
| 575,451 A | * | 1/1897 | Yost |
| 3,991,750 A | | 11/1976 | Vickery |
| 3,995,617 A | | 12/1976 | Watkins et al. |
| 4,148,469 A | * | 4/1979 | Geyer ........................... 267/4 |
| 4,307,722 A | | 12/1981 | Evans |
| 4,503,569 A | | 3/1985 | Dotter |
| 4,546,499 A | | 10/1985 | Possis |
| 4,562,597 A | | 1/1986 | Possis et al. |
| 4,580,568 A | | 4/1986 | Gianturco |
| 4,582,181 A | | 4/1986 | Samson |

(List continued on next page.)

FOREIGN PATENT DOCUMENTS

| | | |
|---|---|---|
| DE | 19703482 | 1/1997 |
| DE | 29619029 | 4/1997 |

(List continued on next page.)

OTHER PUBLICATIONS

A. Hassan Khazei et al., "Myocardial Canalization, A new Method of Myocardial Revascularization", *The Annals of Thoracic Surgery*, vol. 6, No. 2, pp. 163–171, Aug. 1968.

(List continued on next page.)

*Primary Examiner*—Sharon Kennedy
(74) *Attorney, Agent, or Firm*—Kirkpatrick & Lockhart LLP

(57) ABSTRACT

Implants and associated delivery systems for promoting angiogenesis in ischemic tissue are provided. The implants may be delivered percutaneously, thoracically or surgically and are particularly well suited for implantation into the myocardium of the heart. The implants are configured to have a first configuration having a low profile and an expanded, second configuration having a large profile. The implants are delivered to the ischemic tissue location in the first configuration, implanted then expanded to the second configuration. The expanded implants maintain a stress on the surrounding tissue, irritating and slightly injuring the tissue to provoke an injury response that results in angiogenesis. The flow of blood from the surrounding tissue into the implant and pooling of the blood in and around the implant leads to thrombosis and fibrin growth. This healing process leads to angiogenesis in the tissue surrounding the implant. Additionally, the implants may contain an angiogenic substance or a thrombus of blood, preloaded or injected after implantation to aid in initiating angiogenesis.

15 Claims, 17 Drawing Sheets

U.S. PATENT DOCUMENTS

| | | |
|---|---|---|
| 4,641,653 A | 2/1987 | Rockey |
| 4,649,922 A | 3/1987 | Wiktor |
| 4,655,771 A | 4/1987 | Wallsten |
| 4,658,817 A | 4/1987 | Hardy et al. |
| 4,665,918 A | 5/1987 | Garza et al. |
| 4,681,110 A | 7/1987 | Wiktor |
| 4,733,665 A | 3/1988 | Palmaz |
| 4,768,507 A | 9/1988 | Fischell et al. |
| 4,774,949 A | 10/1988 | Fogarty |
| 4,813,925 A | 3/1989 | Anderson, Jr. et al. |
| 4,861,330 A | 8/1989 | Voss |
| 4,889,137 A | 12/1989 | Kolobow |
| 4,904,264 A | 2/1990 | Scheunemann |
| 4,917,666 A | 4/1990 | Solar et al. |
| 4,920,980 A | 5/1990 | Jackowski |
| 4,950,227 A | 8/1990 | Savin et al. |
| 4,969,458 A | 11/1990 | Wiktor |
| 4,994,071 A * | 2/1991 | MacGregor ............... 606/194 |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |
| 5,047,028 A | 9/1991 | Qian |
| 5,049,138 A | 9/1991 | Chevalier et al. |
| 5,056,517 A | 10/1991 | Fenici |
| 5,087,243 A | 2/1992 | Avitall |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A | 12/1992 | Tessmann et al. |
| 5,176,626 A | 1/1993 | Soehendra |
| 5,180,366 A | 1/1993 | Woods |
| 5,190,058 A | 3/1993 | Jones et al. |
| 5,203,546 A * | 4/1993 | Amadore ................ 267/168 |
| 5,256,146 A | 10/1993 | Ensminger et al. |
| 5,266,073 A | 11/1993 | Wall |
| 5,287,861 A | 2/1994 | Wilk |
| 5,290,295 A | 3/1994 | Querals et al. |
| 5,312,456 A | 5/1994 | Reed et al. |
| 5,324,325 A | 6/1994 | Moaddeb |
| 5,366,493 A | 11/1994 | Scheiner et al. |
| 5,372,600 A | 12/1994 | Beyar et al. |
| 5,380,316 A | 1/1995 | Alta et al. |
| 5,389,096 A | 2/1995 | Alta et al. |
| 5,391,199 A | 2/1995 | Ben-Haim |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman et al. |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Haim |
| 5,482,261 A * | 1/1996 | Ortega ................ 267/168 |
| 5,487,739 A | 1/1996 | Aebischer et al. |
| 5,514,176 A | 5/1996 | Bosley, Jr. et al. |
| 5,551,427 A | 9/1996 | Altman |
| 5,551,954 A | 9/1996 | Buscemi et al. |
| 5,562,619 A | 10/1996 | Mirarchi et al. |
| 5,562,922 A | 10/1996 | Lambert |
| 5,569,272 A | 10/1996 | Reed et al. |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,614,206 A | 3/1997 | Randolph et al. |
| 5,628,783 A * | 5/1997 | Quiachon et al. ............... 623/1 |
| 5,643,308 A | 7/1997 | Markman |
| 5,653,756 A | 8/1997 | Clarke et al. |
| 5,655,548 A | 8/1997 | Nelson |
| 5,662,124 A | 9/1997 | Wilk |
| 5,669,924 A * | 9/1997 | Shaknovich ................ 606/108 |
| 5,676,850 A | 10/1997 | Reed et al. |
| 5,690,643 A | 11/1997 | Wijay |
| 5,692,737 A * | 12/1997 | Perlsweig ................ 267/168 |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,762,600 A | 6/1998 | Bruchman et al. |
| 5,769,843 A | 6/1998 | Abela et al. |
| 5,782,823 A | 7/1998 | Mueller |
| 5,785,702 A | 7/1998 | Murphy-Chutorian et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,824,049 A | 10/1998 | Ragheb et al. |
| 5,824,071 A | 10/1998 | Nelson et al. |
| 5,830,502 A | 11/1998 | Dong et al. |
| 5,840,059 A | 11/1998 | March et al. |
| 5,851,228 A * | 12/1998 | Pinheiro ................ 623/1 |
| 5,861,032 A | 1/1999 | Subramaniam |
| 5,879,383 A | 3/1999 | Bruchman et al. |
| 5,893,869 A | 4/1999 | Barnhart et al. |
| 5,899,915 A | 5/1999 | Saadat |
| 5,971,993 A | 10/1999 | Hussein |
| 5,980,514 A | 11/1999 | Kupiecki et al. |
| 5,980,548 A | 11/1999 | Evans et al. |
| 6,033,434 A | 3/2000 | Borghi |
| 6,045,565 A | 4/2000 | Ellis et al. |
| 6,053,924 A | 4/2000 | Hussein |
| 6,086,611 A * | 7/2000 | Duffy et al. ................ 623/1 |
| 6,099,560 A * | 8/2000 | Penn et al. ................ 623/1.35 |
| 6,197,049 B1 * | 3/2001 | Shaolian et al. ............ 623/1.35 |
| 6,197,324 B1 | 3/2001 | Crittenden |
| 6,248,112 B1 | 6/2001 | Gambale et al. |
| 6,251,418 B1 | 6/2001 | Ahern et al. |
| 6,263,880 B1 | 7/2001 | Parker et al. |
| 6,277,082 B1 | 8/2001 | Gambale |
| 6,395,022 B1 * | 5/2002 | Piplani et al. ............. 623/1.35 |
| 6,432,126 B1 | 8/2002 | Gambale et al. |
| 6,447,522 B2 | 9/2002 | Gambale et al. |

FOREIGN PATENT DOCUMENTS

| | | |
|---|---|---|
| EP | 0 515 867 A2 | 12/1992 |
| EP | 0 490 459 A1 | 10/1994 |
| EP | 0 714 640 A1 | 6/1996 |
| EP | 0 717 969 A2 | 6/1996 |
| EP | 0 732 089 A2 | 9/1996 |
| EP | 0 812 574 A2 | 12/1997 |
| EP | 0 830 873 A2 | 3/1998 |
| EP | 0 853 921 A2 | 7/1998 |
| EP | 0 953 320 A2 | 11/1999 |
| FR | 1514319 | 1/1967 |
| FR | 2725615 | 10/1994 |
| RU | 2026640 C1 | 1/1995 |
| RU | 2063179 C1 | 7/1996 |
| WO | WO 89/01798 | 3/1989 |
| WO | WO 91/15254 | 10/1991 |
| WO | WO 94/05265 | 3/1994 |
| WO | WO 94/27612 | 12/1994 |
| WO | WO 96/20698 | 7/1996 |
| WO | WO 97/42910 | 7/1997 |

| | | |
|---|---|---|
| WO | WO 97/32551 | 9/1997 |
| WO | WO 97/38730 | 10/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |

OTHER PUBLICATIONS

Alfred Goldman et al., "Experimental Methods for Producing a Collateral Circulation to the Heart Directly from the Left Ventricle", *Journals of Thoracic Surgery*, vol. 31, No. 3, pp. 364–374, Mar. 1956.

A. Sachinopoulou et al., "Invited Review Transmyocardial Revascularization", *Lasers in Medical Science*, vol. 10, pp. 83–91, Sep. 1995.

B. Schumacher et al., Induction of Neoangiogenesis in Ischemic Myocardium by Human Growth Factors, First Clinical Results of a New Treatment of Coronary Heart Disease, Clinical Investigation and Reports, pp. 645–650, Dec. 1997.

Charles T. Dotter, Transluminally–placed Coilspring Endarterial Tube Grafts: Long–term Patency in Canine Popliteal Artery, Investigative Radiology, pp. 329–332, Sep.–Oct. 1969.

C. Massimo, et al., Myocardial Revascularization By a New Method of Carrying Blood Directly from the Left Ventricular Cavity into the Coronary Circulation, Journals of Thoracic Surgery, vol. 34, No. 2, pp. 257–264, Aug. 1957.

Garrett Lee et al., Feasibility of Intravascular Laser Irradiation for In vivo Visualization and therapy of Cardiocirculatory Diseases, American Heart Journal., vol. 103 No. 6, pp. 1076–1077.

Garrett Lee et al., Laser–Dissolution of Coronary Atherosclerotic Obstruction, American Heart Journal, vol. 102 No. 6, part 1, pp. 1074–1075, Dec. 1981.

George S. Abela et al., Use of Laser Radiation to Recanalize Totally Obstructed Coronary Arteries (Abstract), Journal American College Cardiology 1983:1(2):691.

George S. Abela et al., Laser Revascularization: What Are Its Prospects?, Journal of Cardiovascular Medicine, pp. 977–984, Sep. 1983.

Isam N. Anabtawi et al., Experimental Evaluation of Myocardial Tunnelization as a Method of Myocardial Revascularization, Journal of Thoracic and Cardiovascular Surgery, vol. 58, No. 5, pp. 638–646, Nov. 1969.

John E. Hershey et al., Transmyocardial Puncture Revascularization, Geriatrics, pp. 101–108, Mar. 1969.

Ladislav Kuzela et al. Experimental Evaluation of Direct Transventricular Revascularization, Journal of Thoracic Cardiovascular Surgery, vol. 57, No. 6, pp. 770–773, Jun. 1969.

Mahmood Mirhoseini et al., Myocardial Revascularization by Laser: A Clinical Report; Lasers in Surgery and Medicine 3:241–245 (1983).

Mahmood Mirhoseini et al., Revascularization of the Heart by Laser; Journal of Microsurgery, pp. 253–260, Jun. 1981.

Mahmood Mirhoseini et al., Transventricular Revascularization by Laser, Lasers in Surgery and Medicine, vol., 2, pp. 1987–198, 1982.

Mahmood Mirhoseini et al., Clinical Report: Laser Myocardial Revascularization, Lasers in Surgery and Medicine vol., 6, pp. 459–461, 1986.

Mahmood Mirhoseini et al., New Concepts in Revascularization of the Myocardium, The Annals of Thoracic Surgery, vol. 45, No. 4, pp. 415–420, Apr. 1988.

P. Walter et al., Treatment of Acute Myocardial Infarction by Transmural Blood Supply from the Ventricular Cavity, Department of Surgery and Department of Radiology of the Hanover Medical School, Hanover, pp. 130–138, (1971).

Peter Whittaker, et al., Transmural Channels Can Protect Ischemic Tissue, Assessment of Long–term Myocardial Response to Laser and Needle–Made Channels, Circulation, vol. 93, No. 1, pp. 143–152, Jan. 1996.

P.K. Sen. et al., Further Studies in Multiple Transmyocardial Acupuncture as a Method of Myocardial Revascularization, Surgery, vol., 64, No. 5, pp. 861–870, No. 1968.

P.K. Sen, et al, Transmyocardial Acupuncture, A New Approach to Myocardial Revascularization; Journal of Thoracic and Cardiovascular Surgery, vol. 50, No. 2, pp. 181–189, Aug. 1965.

R.I. Hardy et al., Regional Myocardial Blood Flow and Cardiac Mechanics in Dog Hearts with $CO_2$ Laser–Induced Intramyocardial Revascularization, Basic Research Cardiology, 85:179–197 (1990).

Roque Pifarre et al., Myocardial Revascularization by Transmyocardial Acupuncture: A Physiologic Impossibility; Journal of Thoracic and Cardiovascular Surgery; vol. 58, No. 3, pp. 424–429, Sep. 1969.

Valluvan Jevanandam et al., Myocardial Revascularization by Laser–Induced Channels, Surgical Forum vol. VL, American College of Surgeons $76^{th}$ Clinical Congress, vol. 4, pp. 225–227, Oct. 1990.

Neil B. Ingels, et al., Measurement of Midwall Myocardial Dynamics in Intact Man by Radiography of Surgically Implanted Markers, Circulation, vol. 52, pp. 859–867 (Nov. 1975).

U.S. patent application Ser. No. 09/073,118, Gambale, filed May. 05, 1998.

U.S. patent application Ser. No. 6,689,121, filed Feb. 10, 2004.

U.S. patent application Ser. No. 09/162,547, Gambale, filed Sep. 29, 1998.

U.S. patent application Ser. No. 6,692,520, Gambale et al., filed Feb. 17, 2004.

U.S. patent application Ser. No. 6,620,170, Ahern, filed Sep. 16, 2003.

U.S. patent application Ser. No. 6,719,805, Ahern, filed Apr. 13, 2004.

U.S. patent application Ser. No. 09/368,119, Tedeschi et al., filed Aug. 04, 1999.

U.S. patent application Ser. No. 09/743,695, Weiser et al., filed Apr. 12, 2001.

U.S. patent application Ser. No. 09/743,726, Gambale et al., filed Apr. 12, 2001.

U.S. patent application Ser. No. 6,709,425, Gambale et al., filed Mar. 23, 2004.

U.S. patent application Ser. No. 2001/0033867, Ahern et al., filed Jun. 25, 2001.

U.S. patent application Ser. No. 2002/0032476, Gambale et al., filed Nov. 21, 2001.

U.S. patent application Ser. No. 10/048,205, Gambale, filed May. 02, 2002.

U.S. patent application Ser. No. 10/048,694, Gambale et al., filed Jun. 10, 2002.

* cited by examiner

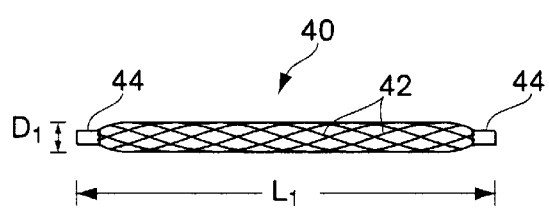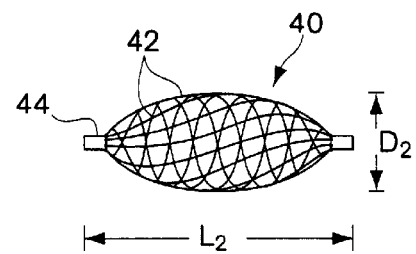
Fig. 5A  Fig. 5B
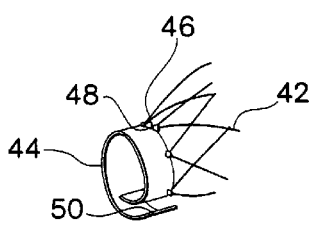
Fig. 5C
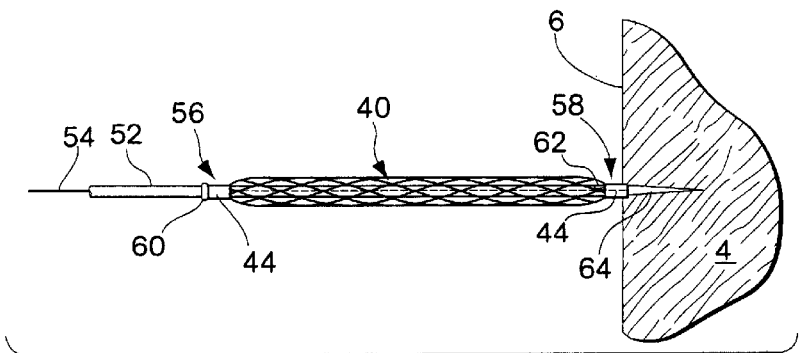
Fig. 6A
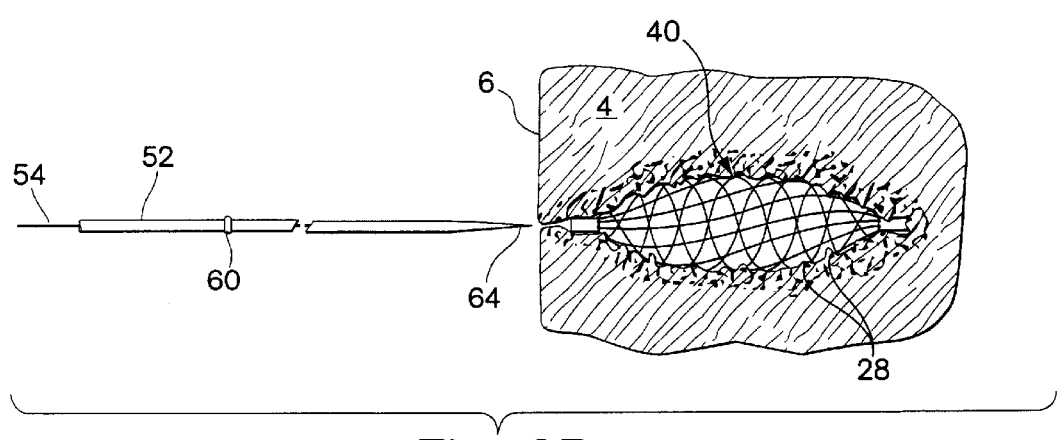
Fig. 6B

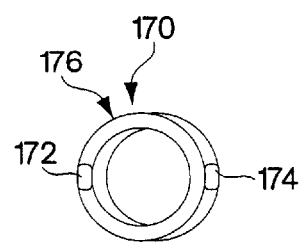
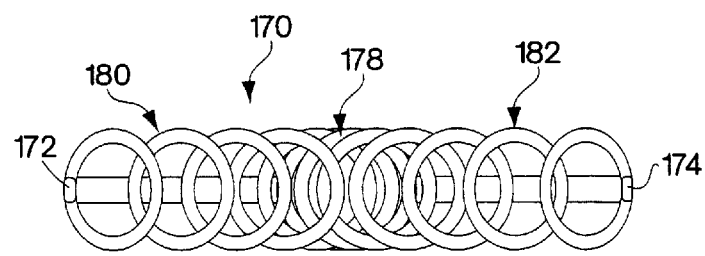
Fig. 17A    Fig. 17B
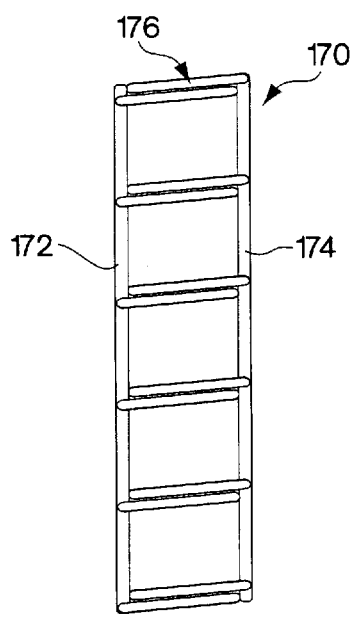
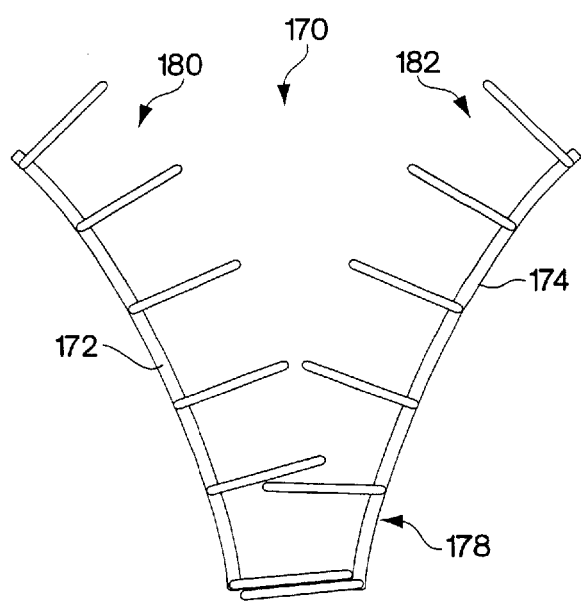
Fig. 17C    Fig. 17D

VASCULAR INDUCING IMPLANTS

RELATED APPLICATION

This application is a continuation of application Ser. No. 09/164,173 filed Sep. 30, 1998, now U.S. Pat. No. 6,458,092, issued Oct. 1, 2002.

FIELD OF THE INVENTION

This invention relates to methods and devices for inducing angiogenesis in ischemic tissue.

BACKGROUND OF THE INVENTION

Tissue becomes ischemic when it is deprived of oxygenated blood. Blood may be present in such tissue, though it is not carrying oxygen. Ischemic tissue can be revived to function normally if it has remained viable despite the deprivation of oxygenated blood. Ischemia can be caused by a blockage in the vascular system that prohibits oxygenated blood from reaching the affected tissue area. Ischemia causes pain in the area of the affected tissue and in the case of muscle tissue can interrupt muscular function.

Although ischemia can occur in various regions of the body, often tissue of the heart, the myocardium, is affected by ischemia due to coronary artery disease, occlusion of the coronary artery, which otherwise provides blood to the myocardium. Muscle tissue affected by ischemia can cause pain to the individual affected. Ischemia can be treated, if a tissue has remained viable despite the deprivation of oxygenated blood, by restoring blood flow to the affected tissue.

Treatment of myocardial ischemia has been addressed by several techniques designed to restore blood supply to the affected region. Coronary artery bypass grafting CABG involves grating a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery,* Vol. 50, No. 2, August 1965, pp. 181–189. Although others have reported varying degrees of success with various methods of piercing the myocardium to restore blood flow to the muscle, many have faced common problems such as closure of the created channels. Various techniques of perforating the muscle tissue to avoid closure have been reported by researchers. These techniques include piercing with a solid sharp tip wire, hypodermic tube and physically stretching the channel after its formation. Reportedly, many of these methods still produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularization of the Heart by Laser", *Journal of Microsurgery,* Vol. 2, No. 4, June 1981, pp. 253–260. The laser was said to form channels in the tissue that were clean and made without tearing and trauma, suggesting that scarring does not occur and the channels are less likely to experience the closure that results from healing. Aita U.S. Pat. Nos. 5,380,316 and 5,389,096 disclose another approach to a catheter based laser system for TMR.

Although there has been some published recognition of the desirability of performing transmyocardial revascularization (TMR) in a non-laser catheterization procedure, there does not appear to be evidence that such procedures have been put into practice. For example, U.S. Pat. No. 5,429,144 Wilk discloses inserting an expandable stent within a preformed channel created within the myocardium for the purposes of creating blood flow into the tissue from the left ventricle Performing TMR by placing stents in the myocardium is also disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open a channel in the myocardium through which blood enters from the ventricle and perfuses into the myocardium.

Angiogenesis, the growth of new blood vessels in tissue, has been the subject of increased study in recent years. Such blood vessel growth to provide new supplies of oxygenated blood to a region of tissue has the potential to remedy a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation,* 1998; 97:645–650. The authors noted that such treatment could be an approach to management of diffused coronary heart disease after alternative methods of administration have been developed.

SUMMARY OF THE INVENTION

The vascular inducing implants of the present invention provide a mechanism for initiating angiogenesis within ischemic tissue. The implants interact with the surrounding tissue in which they are implanted and the blood that is present in the tissue to initiate angiogenesis by various mechanisms.

Primarily, it is expected that the implants will trigger angiogenesis in the ischemic tissue by interacting in one or more ways with the tissue to initiate an injury response. The body's response to tissue injury involves thrombosis formation at the site of the injury or irritation. Thrombosis leads to arterioles and fibrin growth which is believed to ultimately lead to new blood vessel growth to feed the new tissue with blood. The new blood vessels that develop in this region also serve to supply blood to the surrounding area of ischemic tissue that was previously deprived of oxygenated blood.

The implant devices may be formed in a variety of configurations to carry out the objectives outlined above for initiating angiogenesis. Specifically, the implants can be arranged in various ways to provide a first configuration that presents a reduced profile and a second configuration that is expanded to provide a larger profile that will irritate and place stress on the surrounding tissue into which it has been implanted. The first configuration is suitable for delivery to the tissue site and into the tissue. The second configuration is obtained after the implant is placed in the tissue. Expansion of the device to the larger profile configuration not only places stress on the tissue but serves to rupture and injure the tissue slightly as it expands. The change in profile between the first configuration and second configuration is of such a magnitude that the irritation and injury suffered by surrounding tissue upon expansion of the implant will induce an injury response that results in angiogenesis. However, the magnitude of the expansion to the second configuration is not so great that tissue becomes severely injured: function impaired and unable to heal.

Additionally, each implant embodiment serves to provide a constant source of irritation and injury to the tissue in which it is implanted, thereby initiating the healing process in that tissue that is believed to lead to angiogenesis. As tissue surrounding the implant moves, such as the contraction and relaxation of muscle tissue, some friction and abrasion from the implant occurs, which injures the tissue. The injury caused by the outside surfaces of the implants to the surrounding tissue does not substantially destroy the tissue, but is sufficient to initiate an injury response and healing which leads to angiogenesis.

Implant embodiments of the invention also serve to initiate angiogenesis by providing an interior chamber into which blood may enter, collect and thrombose. Blood that enters the implant and remains, even temporarily, tends to coagulate and thrombus. Over time, continued pooling of the blood in the interior will cause thrombosis and fibrin growth throughout the interior of the implant and into the surrounding tissue. New blood vessels will grow to serve the new growth with oxygenated blood, the process of angiogenesis.

Implant embodiments may further be prepared to initiate angiogenesis by having a thrombus of blood associated with them at the time of their implantation or inserted in the interior immediately following implantation. The thrombus of blood may be taken from the patient prior to the implant procedure and is believed to help initiate the tissue's healing response which leads to angiogenesis.

Alternatively or in addition to a thrombus of blood, the implant devices may be associated with an angiogenic substance in a variety of ways to aid the process of angiogenesis, In embodiments having a defined interior, the substance may be placed within the interior prior to implantation or injected after the implantation of the device. The substance may be fluid or solid. The blood flow into and interacting with the interior of the device will serve to distribute the substance through the surrounding tissue area because blood entering the device mixes with and then carries away the substance as it leaves the device. Viscosity of the substance and opening size through which it passes, determine the time-release rate of the substance.

Substances may be associated with the device, not only by being carried within their interiors, but also by application of a coating to the device. Alternatively, the substance may be dispersed in the composition of the device material. Alternatively, the implant may be fabricated entirely of the angiogenic substance. Recognizing that there are many ways to attach an angiogenic substance or drug to a device, the methods listed above are provided merely as examples and are not intended to limit the scope of the invention. Regardless of the method of association, the implants of the present operation operate to distribute the angiogenic substance in surrounding tissue by the implants contact with the tissue and blood supply in that tissue area.

By way of example, the implant device may comprise a helical spring having a first configuration that is more tightly wound, having an elongated length, more coils and a reduced diameter The second configuration of the spring will provide an increased profile by increasing the diameter of the coils through shortening the length of the spring.

In another embodiment, the implant may comprise a mesh tube comprised of individual wire-like elements that are woven and arranged to allow the tube to have a first configuration that is elongated with a smaller diameter and a second configuration that is shortened in length, but correspondingly larger in diameter and profile. In yet another configuration, the implant may comprise a sheet of solid or porous material that is rolled into a tube. A first, reduced profile configuration of the tube is tightly rolled upon itself, storing potential energy that will provide resilient expansion of the rolled tube to a less tightly rolled tubular shape when released. The expanded configuration of the tube provides a second configuration of the implant that has a larger profile. In another embodiment, the implant may comprise a spine having spaced along its length several C-shaped rings that may be compressed into a smaller profile in which the rings are closed and a second configuration having an increased profile wherein the rings are opened to a C-shape. The ends of the C-shaped rings may be formed to have eyelets that meet and are concentrically arranged when the rings are closed so that a release pin can be inserted through them to hold them in their reduced profile configuration. Once the implant is placed within the tissue, the release pin may be removed permitting the rings to resiliently expand to a C configuration.

In another embodiment, the implant may have a first configuration that is uniaxial and a second configuration that is biaxial or bifurcated to provide an increased profile. The bifurcated embodiments disclosed may be comprised of single or double helical coils arranged to have a trunk portion and two leg portions. The resulting appearance is similar to a pair of pants. Alternatively, the bifurcated embodiment may be configured as two spines having loops mounted concentrically along their length, the spines being joined to several common loops at one end to form a trunk portion, and the other ends of the spine being free to form the leg portions of the implant. In both bifurcated implant embodiments, the loops or coils are interleaved while maintained in the first configuration such that they lie substantially along the same axis. In the second configuration, the spines spring apart to form a Y-shaped or bifurcated configuration presenting a larger profile to increase the injury to surrounding tissue and initiate angiogenesis.

Alternatively, the device may comprise a body that has attached thereto flexible elements configured to retain, at least temporarily, blood or angiogenic substances. An example of such an embodiment would be a small brush having an axial core member with a plurality of flexible bristles extending radially therefrom. The bristles having a natural resilience to a radially outward configuration with respect to the core. During delivery of the brush into tissue, the bristles are swept back against the core. However, after insertion, the resilient bristles return at least partially to their radially outward extending configuration, thereby placing surrounding tissue in stress and causing irritation to the tissue. The bristles are also configured to absorb, or hold within a hollow interior a drug or amount of quantity of blood. Additionally, the core member may be configured to define a hollow interior capable of holding a therapeutic substance.

One or more implants of the present invention may be applied to an area of ischemic tissue. By way of example, the implants may define a width of approximately 2 mm and a length corresponding to somewhat less than the thickness of the tissue into which it is implanted. It is anticipated that implants having a 2 mm wide profile would serve an area of ischemic tissue of approximately one square centimeter to adequately promote angiogenesis throughout the surrounding region of tissue yet avoid altering the movement of the tissue due to a high density of foreign objects within a confined region of tissue.

The implants are delivered directly into the subject tissue without preforming a channel by removal of tissue such as by coring or ablation by a laser. The delivery devices, while loaded with the implant, operate to pierce and penetrate the tissue in a single driving motion. While the delivery device is penetrating the tissue, the implant is released and expanded into its second configuration within the tissue. The expanded implant is left behind as the delivery device is withdrawn. Upon expansion of the device, the surrounding tissue may tear and become injured as it is pushed aside by the implant. The stressed tissue also tries to recoil around the device and may herniate through openings in the structure of the device. It is not important that the implant maintain an open channel through the tissue for blood to flow. The objective of the implant is to trigger angiogenesis, so that new blood vessels will be created to introduce blood flow to the region.

The devices may be implanted percutaneously and transluminally, thoracically or surgically by a cut down method. In the case of implants placed within myocardial tissue of the heart, delivery systems are disclosed for percutaneously accessing the left ventricle of the heart and penetrating and delivering the implant into the myocardium.

It is an object of the present invention to provide a method of promoting angiogenesis within ischemic tissue.

It is another object of the present invention to provide a method of promoting angiogenesis by implanting a device within ischemic tissue.

It is another object of the present invention to provide a method of promoting angiogenesis by causing thrombosis in the area of ischemic tissue.

It is another object of the present invention to provide a process of promoting angiogenesis within ischemic myocardial tissue of the heart.

It is another object of the invention to provide an implant suitable for implantation within tissue of the human body.

It is another objective of the present invention to provide an implant delivery system that is safe and simple to use while minimizing trauma to the patient.

It is another object of the invention to provide an implant that will irritate tissue that surrounds the implant to initiate a healing response that leads to angiogenesis.

It is another object of the invention to provide an implant having a small profile first configuration and large profile second configuration after implantation into tissue such that the implant places stress on the surrounding tissue.

It is another object of the invention to provide an implant that is configured to have associated with it an angiogenic substance that promotes angiogenesis within tissue surrounding the implant.

It is another object of the invention to provide an implant configured to interact with blood present in the tissue into which the implant is inserted.

It is another object of the invention to provide an implant that defines an interior into which blood can enter and thrombose.

It is another object of the invention to provide an implant to which a thrombus of blood or an angiogenic substance can be inserted before or after the implant has been inserted into tissue.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 5A shows a side view of a mesh tube implant in its low profile first configuration;

FIG. 5B shows a side view of a mesh tube implant in its large profile second configuration;

FIG. 5C shows a detailed view of the band of the mesh tube embodiment;

FIG. 6A shows a side view of the mesh tube embodiment in its low profile first configuration being delivered into a tissue location;

FIG. 6B shows a sectional illustration of the mesh tube implant its large profile, second configuration residing within tissue;

FIG. 17A is a top view of a bifurcated spine and hoop implant in its low profile first configuration;

FIG. 17B is a top view of a bifurcated spine and hoop implant in its large profile second configuration;

FIG. 17C is a side view of a bifurcated spine and hoop implant in its low profile first configuration;

FIG. 17D is a side view of a bifurcated spine and hoop implant in its large profile second configuration;

DESCRIPTION OF THE ILLUSTRATIVE EMBODIMENT

Figure 1A:
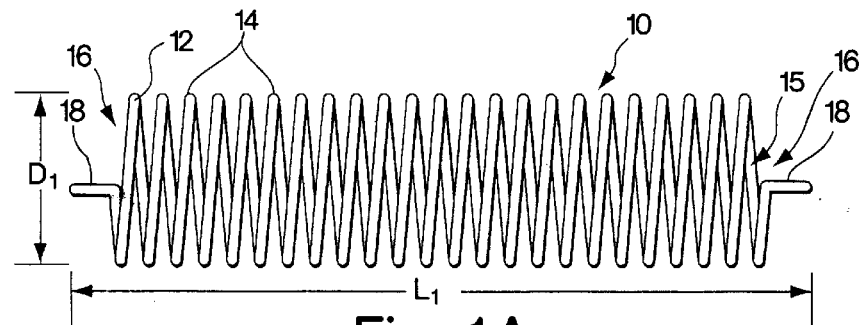
FIG. 1A shows a side view of a spring implant embodiment in its small profile, first configuration.
Figure 1B:
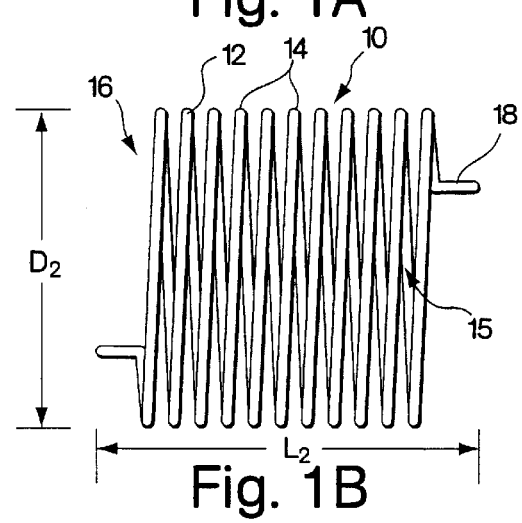
FIG. 1B shows a side view of a spring implant embodiment in its large profile second configuration.
Figure 1C:
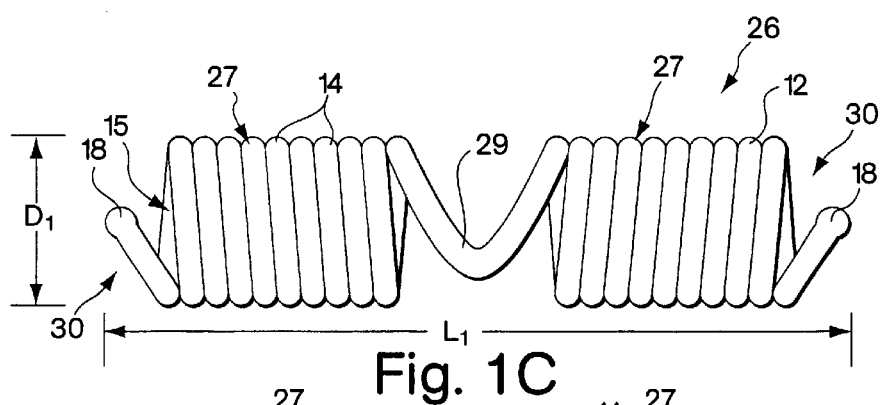
FIG. 1C shows an alternate spring implant embodiment in its small profile first configuration.
Figure 1D:
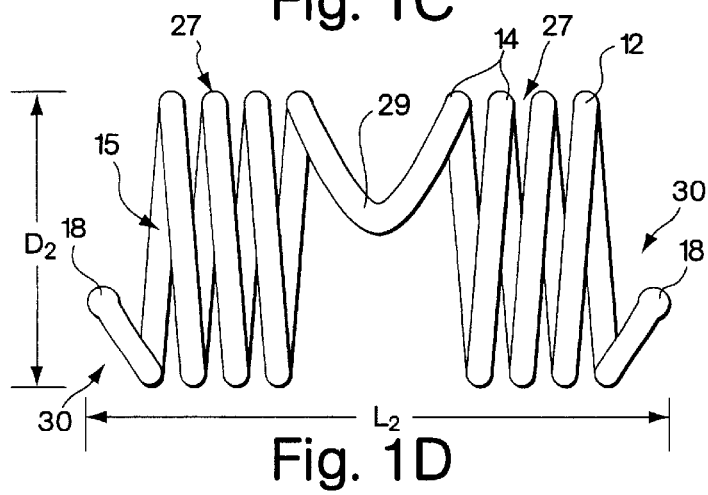
FIG. 1D shows an alternate spring implant embodiment in its large profile second configuration.

FIGS. 1A and 1B show a first embodiment of the implant comprising a helical coil spring 10. The spring is formed from a filament 12 of flexible material such as stainless steel or other metal or high density polymer. The filament is helically wrapped to form several individual coils 14 that comprise a spring having an interior 15. At each end 16 of the spring, the filament 12 terminates with a small tab 18 extending in a plane parallel to the axis of the implant. The tabs 18 are used for maintaining the implant upon the delivery device as will be described in further detail below. FIGS. 1C and 1D show an alternative spring implant embodiment 26 comprised of two segments 27 that are wound in opposite directions and joined together by a bridge 29. Each segment has a free end 30 in which the filament 12 terminates in a bulbous tab 18.

The spring implant embodiments are easily arranged from a first configuration to a second configuration, where the second configuration of the implant has a larger profile than that presented while in the first configuration. Profile may be defined as the maximum width, or in the case of a coil, the diameter, of the device. FIGS. 1A and 1C show the device in a small profile, first configuration that is suitable for delivery of the device into the tissue. FIGS. 1B and 1C show the implant devices in a larger profile, second configuration into which the implant is transformed after delivery to place surrounding tissue in stress.

In its first configuration, shown in FIGS. 1A and 1C, the spring is wrapped more tightly, having a longer length $L_1$ and more coils 14 and thus a smaller diameter $D_1$ than in the second configuration shown in FIGS. 1B and 1D. In the second configuration, shown in FIGS. 1B and 1D, the diameter $D_2$ is greater than $D_1$ and $L_2$ is less than $L_1$ because the spring has expanded, becoming less tightly wound and having fewer coils 14. The alternate, double spring embodiment resiliently expands from its restrained first configuration to its larger profile, second configuration more gradually than does the single spring implant 10. The counter rotation of the oppositely wound spring segments 28 serves to slow the unwinding of the device, thereby providing control over the magnitude of injury experienced by the surrounding tissue.

The implant is more easily delivered into the intended tissue location while in the first configuration of FIGS. 1A and 1C. The reduced profile presented by the spring in a smaller diameter $D_1$, on the order of 1.0–1.5 mm, can more easily penetrate tissue. A channel need not be preformed by removing tissue through coring or laser techniques to place the implants. The implants are not intended to maintain a patent channel through the subject tissue through which blood can flow. The implants of the present invention induce angiogenesis by interacting with the tissue and blood already in the area into which they are placed. Once implanted in the tissue, the expansion of the implant to its larger profile, second configuration, on the order of 2.0–2.5 mm, serves not only to help anchor the implant within the tissue, but also serves to irritate and injure the surrounding tissue into which it is implanted. Preferably, the spring embodiments are fabricated to have an unstressed configuration equivalent to the second configuration shown in FIGS. 1B and 1D as this will be the final implanted configuration of the device after release from its delivery device. The expanding implants may rupture and push aside tissue, which permits the inflow and collection of blood from the surrounding area. However, maintaining a patent channel for blood flow through the implant is not necessary.

A more important aspect of the presence of the implants is that injury response exhibited by the surrounding ischemic tissue is maximized and angiogenesis is initiated by the resulting thrombosis and fibrin growth as described above. The implants remain expanded against the surrounding tissue after implantation becoming clotted with thrombosis and fibrin growth throughout the implant structure. After the new tissue has surrounded and ingrown the implant new vessel growth will emerge in the region to supply the new tissue. At this advanced stage of injury response and healing, the stress applied on surrounding tissue by the expanded implant may be minimal or nonexistent because tissue has grown around and accommodated the implant.

Figure 2A:
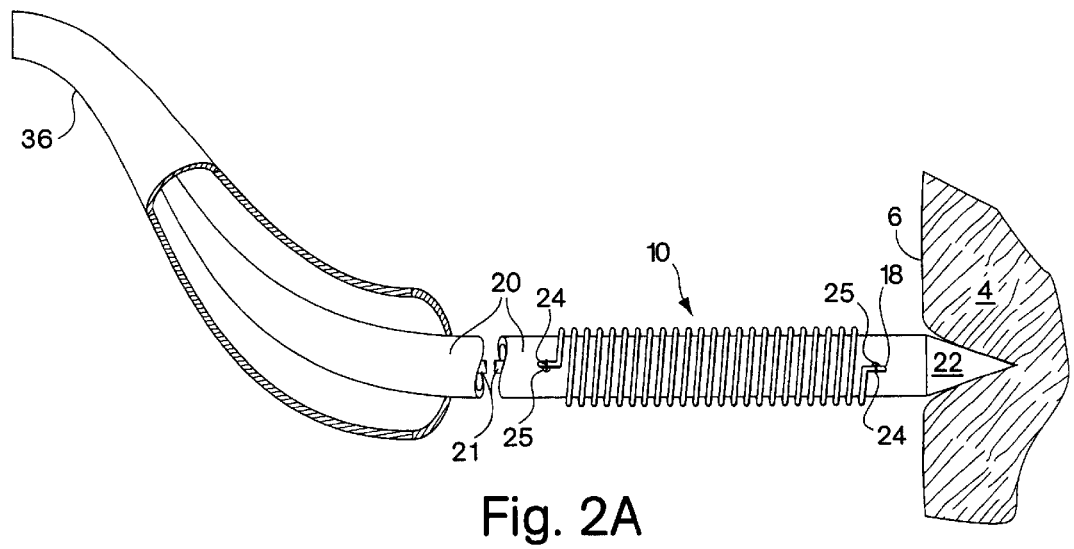
FIG. 2A is a side view of the spring implant embodiment in its low profile, first configuration being delivered to a tissue location.
Figure 2B:
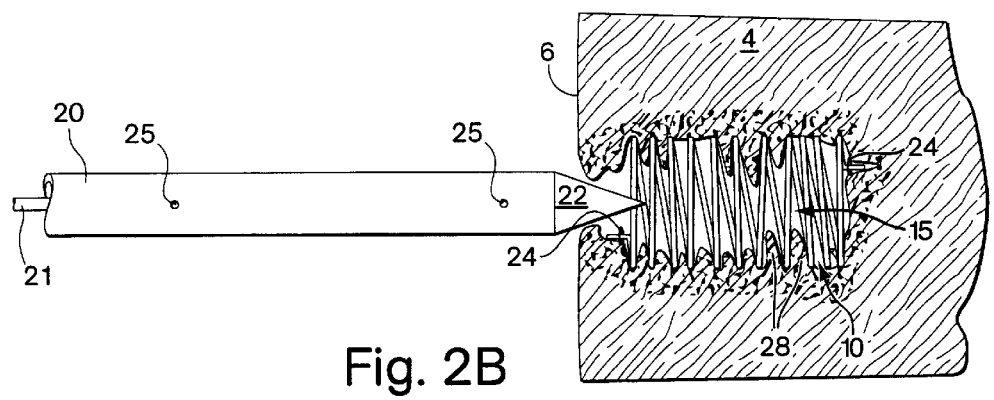
FIG. 2B is a diagrammatical sectional illustration of the implant expanded to its second configuration within a tissue location.
Figure 2C:
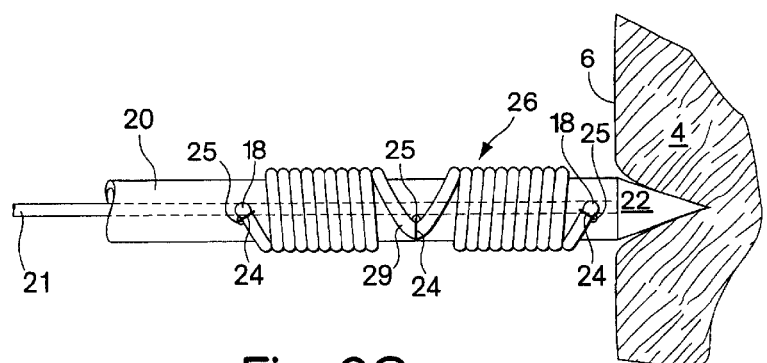
FIG. 2C shows a side view of the alternate spring embodiment mounted on a delivery device.
Figure 3:
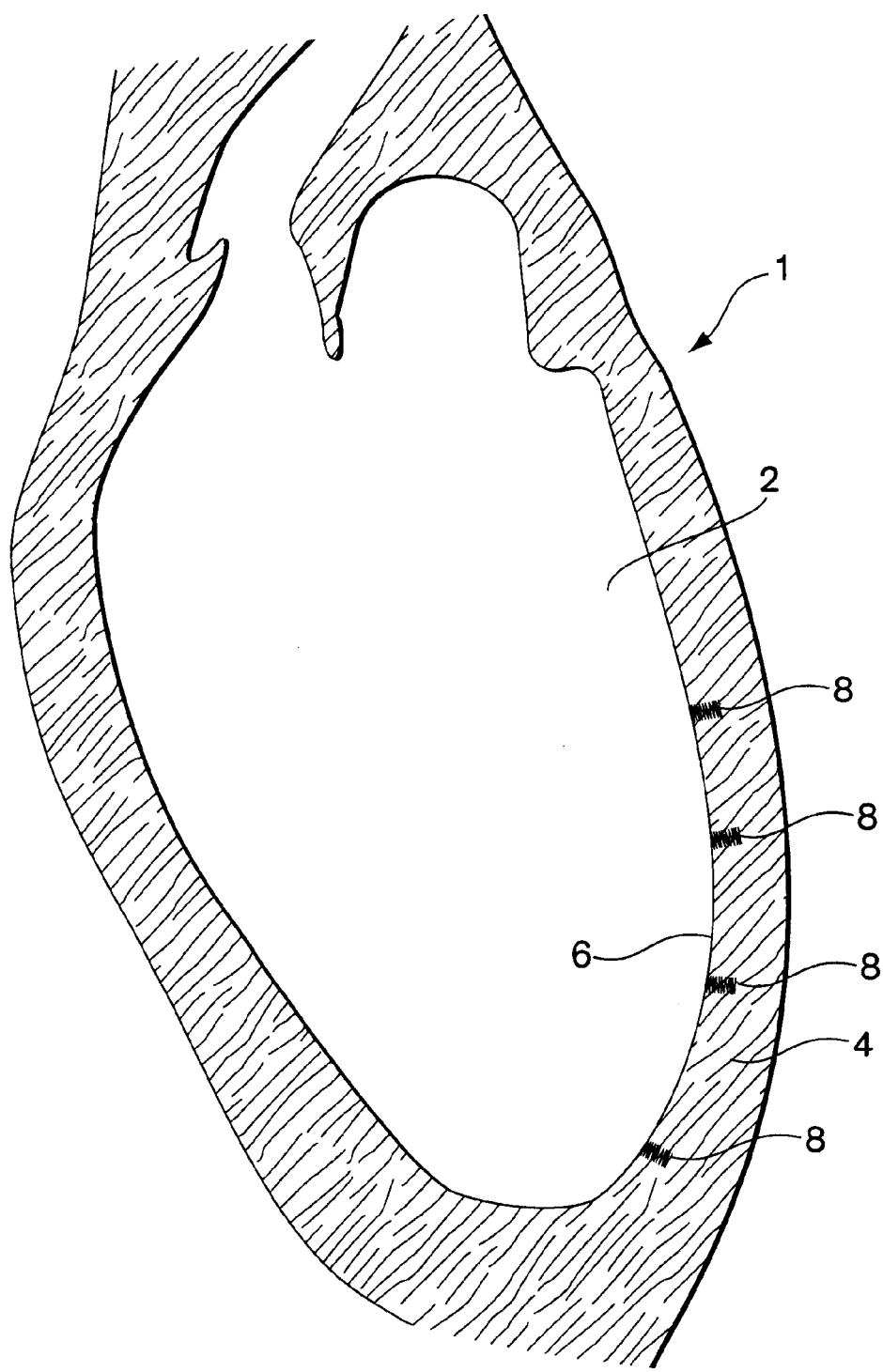
FIG. 3 shows a sectional illustration of the left ventricle of a human heart having several implants of the present invention.
Figure 4A:
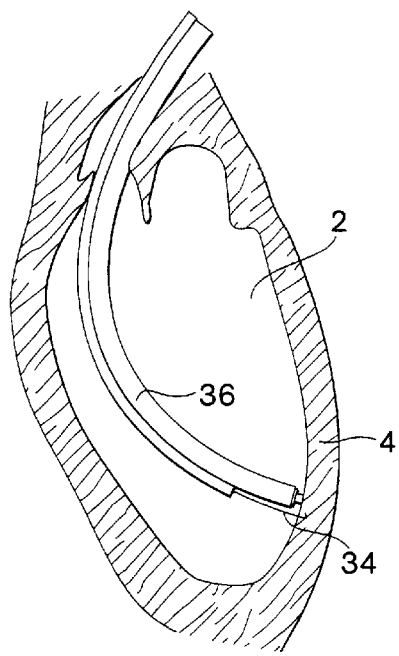
FIGS. 4A–4D show a sectional illustration of the left ventricle of a human heart with a steerable delivery catheter positioned within the ventricle to deliver implants into the myocardium.
Figure 4B:
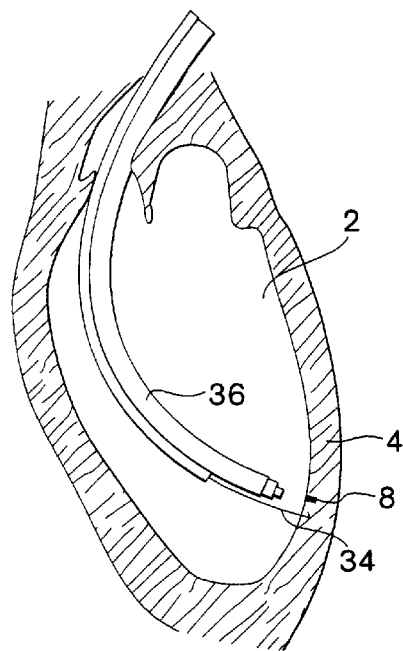
Figure 4C:
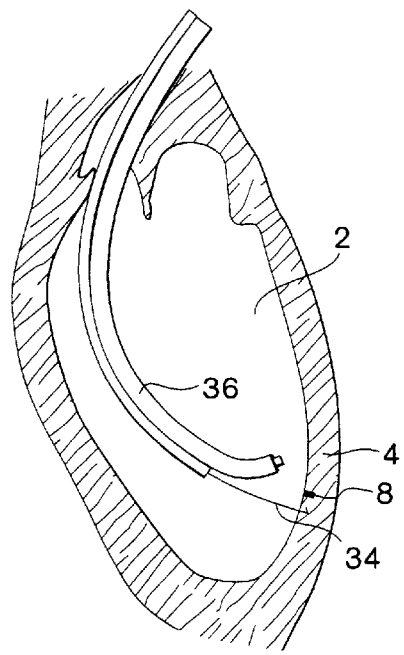
Figure 4D:
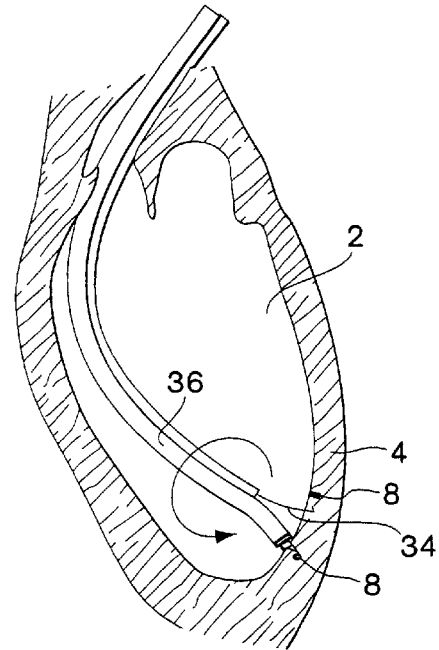

Access to ischemic tissue sites within a patient to deliver the implants of the present invention may be accomplished percutaneously, surgically by a cut-down method orthoracically. However, the less invasive and traumatic percutaneous approach of delivering the implants is generally preferred. A percutaneous delivery device for delivering the implants to the myocardium of the heart is shown in FIGS. 2A–2C. FIG. 3 shows a diagrammatic sectional view of the left ventricle 2 of a human heart 1 into which the delivery device gains access. Each of the implant embodiments described herein may be delivered percutaneously through a delivery catheter 36, shown in FIGS. 4A–4D, as will be described in detail below. It is noted that, throughout the description of the implant embodiments and their associated delivery systems, "proximal" refers to the direction along the delivery pathway leading external to the patient and "distal" refers to the direction along the delivery pathway internal of the patient.

To reach the left ventricle of the heart percutaneously, a guide catheter (not shown) is first navigated through the patient's vessels to reach the left ventricle 2 of the heart 1. A barb tipped guidewire 34 may then be inserted through the guide catheter and into the ventricle where it pierces the myocardium 4 and becomes anchored within the tissue. After anchoring the guidewire, a steerable implant delivery catheter 36 may be advanced over the guidewire to become positioned within the ventricle for delivery of the implants. To facilitate delivery of multiple implants, the guidewire lumen of the delivery catheter 36 may be eccentrically located on the catheter 36. Therefore, when the catheter is rotated about the guidewire, the center of the catheter will rotate through a circular path as demonstrated in FIGS. 4C and 4D, to encompass a broader delivery area with one guidewire placement. The outside diameter of the delivery catheter is preferably less than 0.100 inch. Additionally, the delivery catheter may be provided with steering capability by means of a pull wire extending the length of the catheter and attached at its distal end such that pulling on the wire from the proximal end causes the distal tip of the catheter to be deflected. Steering capability thus provides a broader range of delivery area with a single catheterization. A detailed description of the construction of the steerable delivery catheter 36 for reaching multiple sites within the left ventricle is described in U.S. patent application Ser. No. 09/073,118 filed May 5, 1998, the entirety of which is herein incorporated by reference.

FIGS. 2A and 2B show the delivery of the spring implant 10 into tissue. The implant may be carried to the delivery location over a flexible push tube 20 that is slidable through the steerable delivery catheter 36. FIG. 2C shows the alternate embodiment of the spring implant 26 mounted on the push tube 20. The push tube over which the spring implants are carried may be an elongate flexible hypodermic tube and be configured to have a sharp distal end 22 for piercing the surface of tissue into which the implant will be placed. Additionally, the push tube slidably receives a release wire 21, which extends through thread loops 24 that pass through side holes 25 at the distal end of the push tube 20 and wrap around tabs 18 of the spring. In the case of the alternate embodiment, a thread loop 24 extends from the release wire, through a side hole to capture the bridge 29 as well. By the interlocking of the thread loops with the release wire within the push tube, the ends 16 of the spring are held close to the push tube 20 to maintain a tightly wrapped diameter, extended length, first configuration during delivery of the device into the tissue. The tabs 18 preferably have a bulbous configuration of greater diameter than the filament 12 to prevent the tabs from slipping through the thread loop.

After being advanced through the delivery catheter 36 which has been placed adjacent tissue to be treated, the push wire 20 is advanced distally, independently of the delivery catheter 36, so that the sharp distal tip 22 pierces the tissue, as shown in FIG. 2A. Continued further distal movement of the push wire 20 advances the implant into the tissue where it can be released to assume its second configuration having a greater profile than the first configuration. The depth to which the implant is placed within the tissue is not believed to be a significant factor in the ultimate success of the device, however, placement within the tissue within an area believed to have the most significant amount of vascular activity is desirable. For example in the case of myocardial tissue, it has been observed that areas closer to the endocardial surface are generally more active to create pumping action in the myocardium than are areas closer to the epicardial surface. Therefore, when placing implants in myocardial tissue, placement near the endocardial surface is preferred, though it is not necessary to place the implant flush with the surface. It is understood that an area of active, moving muscle tissue will cause the implants of the present invention to flex, at least slightly with the surrounding tissue during the cardiac cycle.

Once the implant is located within the tissue, release wire 21 is withdrawn proximally relative to the push tube 20. Thread loops become released from the wire 21 and are free to pass through side holes 25 as the spring resiliently expands to its second, large profile configuration, within the tissue. The greater profile and increased diameter of the implant in the second configuration puts an immediate stress on the surrounding tissue causing some tearing. After expansion to the second configuration, the surrounding tissue 4 may tend to herniate into the implant device at herniation points 28 located between the coils 14 of the implant. After implantation, the push tube 20 is withdrawn proximally through the interior 15 of the implant and back into the delivery catheter 36 together with the release wire, and the assembly withdrawn from the patient. The thread loops 24, preferably absorbable suture material, may be left behind, attached to the implant.

In the case of implants placed within myocardial tissue 4 of the heart 1, several implants 8 may be placed within a region of ischemic tissue as shown in FIG. 3. The implants 8 generally expand to a diameter of approximately 2 mm and are preferably spaced so that each implant serves an area of one square centimeter. Though any number of implants may be placed, the density of approximately one per square centimeter is preferred so as not to interfere with the muscular function of the tissue to which they are implanted.

In other words, many implants within a certain area could potentially interfere with the motion of the muscle tissue to the detriment of other necessary functions of that tissue. Multiple implants are delivered to a given tissue location by repeating the steps recited for delivering a single implant.

In addition to inducing an injury response by expanding within the tissue, the implants induce angiogenesis within the surrounding tissue 4 by other mechanisms. One such mechanism is a process of thrombosis of the blood surrounding an implanted device 10 and being permitted to pool within the interior 15 of the device. Blood that pools around the implant or in the implant thrombosis which leads to fibrin growth and nucleation of arterioles that become vessels to supply blood to the healed region. This process may be further enhanced by application of an angiogenic substance to the implant device. The substance may be a solid or fluid placed within the interior 15 of the device before or after delivery of the implant so that it comes into contact with and is distributed by blood entering and surrounding the implant. To deliver the angiogenic substance to the implant after it has been delivered into tissue, the delivery device may be configured as a conduit through which the substance can be transmitted and released into the implant while the delivery device and implant are still associated. In the case of the tubes and catheters discussed above in connection with a percutaneous delivery technique, the angiogenic substance may be advanced from the proximal end of the tube, outside the patient, through the lumen of the tube and expelled from a port at the distal end of the tube and into or around the implanted device. Alternatively, the angiogenic substance may be coated onto the device or the device may be made from such a substance.

Another embodiment of the vascular inducing implants is shown in FIG. 5A. A mesh tube implant 40 is shown in its low profile first configuration, suitable for delivery into tissue. The mesh tube is comprised of a mesh pattern of wire like elements 42 that are formed from a material that is flexible yet sufficiently rigid to maintain an expanded, second configuration having a larger profile than its first configuration. The mesh tube embodiment may be fabricated from a thin metal sheet etched out a pattern of spaces or openings and then rolled and the ends joined to form a tube. Alternatively, the implant may be formed from a fabric such as dacron rolled into a tubular shape. In a preferred embodiment, the braided tube is formed from wire elements 42 woven together to form a tube with the elements slidable relative to each other. The mesh may be resiliently expandable, remaining expanded by the inherent resilience of the material selected, such as highly elastic or high tensile strength material. Alternatively the mesh tube may be plastically deformed to its second configuration, if the elements are formed from a malleable alloy.

In the wire mesh tube embodiment, the wire ends 46 are joined to rings 44. As shown in FIG. 5C the ends 46 of the wire elements 42 may be joined to the end ring 44 at connections 48. The rings 44 may be polymer tubes heat shrunk to the element ends to form the connections. Alternatively, the rings may be stainless steel, connected to the elements by solder joints. The elements may be fabricated to be movable relative to the ring 44. Although not shown, the ends 46 of the elements may be formed to have eyelets that are threaded around a narrow end ring 44. Thus, the elements would be free to adjust their position along the ring during expansion from the first to the second configuration. Additionally, as shown in FIG. 5C, the ring 44 may be non-continuous, having a split 50 across its surface to promote expandability. In this configuration, the ring 44 may provide the supporting force to keep the implant in its expanded second configuration. The split 50 in the ring 44 permits the ring to be coiled into a small configuration for delivery, yet expand and uncoil into a larger configuration.

The ring 44 may be resiliently expandable, whereby its natural tendency is to have an uncoiled configuration and maximum diameter. In this embodiment, the ring is confined in a coiled smaller diameter during delivery to the intended tissue location and is released to uncoil and resiliently expand to its larger configuration once placed in the tissue. The elements 42 join to the rings 44 at both ends of the mesh tube embodiment thus slide into the second, larger profile configuration under the force of the resilient rings 44. Alternatively, the rings 44 may be plastically deformable so that they expand along with the movement of the elements 42 of the mesh tube 40 as the length of the tube is compressed to cause radial expansion.

The mesh tube implant may be delivered over a delivery system comprising a relatively stiff small diameter tube 52, such as a hypotube having slidable within its central lumen a piercing release wire 54 as shown in FIGS. 6A and 6B. In FIG. 6A the mesh tube 40 is supported from longitudinal movement at its proximal end 56 by a stop 60 mounted on the exterior of the hypotube 52. The distal end 58 of the mesh tube is supported from longitudinal movement by a small catch member 62 mounted on the exterior of the release wire 54. Both the catch 62 and the stop 60 engage the rings 44 at the proximal and distal ends of the mesh tube 40. The hypotube 52 and release wire 54 carrying the mesh tube 40 are delivered to the intended tissue location through a previously placed steerable catheter 36 as was described in connection with FIGS. 2A and 2B. The steerable delivery catheter 36 is not shown in FIGS. 6A and 6B but is understood to be part of the delivery system. While tension is applied on the mesh tube by placing slight pressure on the release wire 54 in the distal direction and maintaining pressure on the hypotube 52 in the proximal direction, the mesh tube is maintained in its low profile extended length first configuration. The combination is together moved distally toward the intended tissue location.

In the case of implantation in the myocardium, the sharp piercing distal tip 64 of the release wire 54 penetrates the endocardial surface 6 to provide access to the myocardium 4. After placement of the mesh tube within the myocardium 4, it is expanded to its second configuration by moving the hypotube, which engages the proximal end 56 of the tube, in a proximal direction while moving the catch 62 on the release wire 54 in a proximal direction. Thus the ends 58 and 56 of the mesh tube are moved closer, thereby shortening the length of the tube and causing it to expand radially, placing stress on the surrounding myocardial tissue 4. After expansion of the mesh tube, the release wire 54 may be withdrawn proximally so that its piercing distal tip 64 is within the hypotube 52. The combination can then be withdrawn from the patient without risk of injury to vessels from the sharp tip during withdrawal.

Figure 7A:
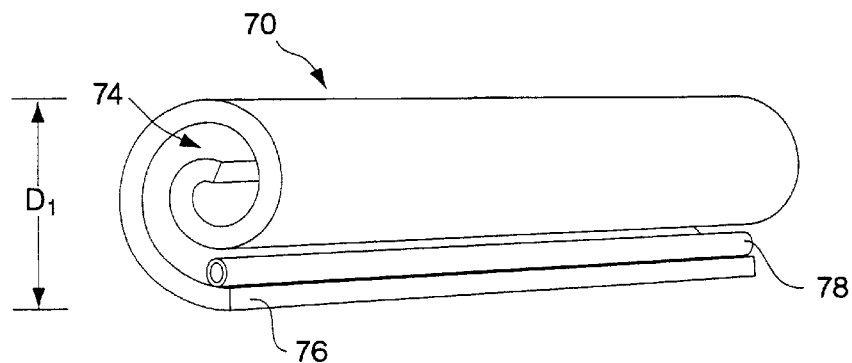
FIG. 7A shows a perspective view of a rolled tube implant in its small profile first configuration.
Figure 7B:
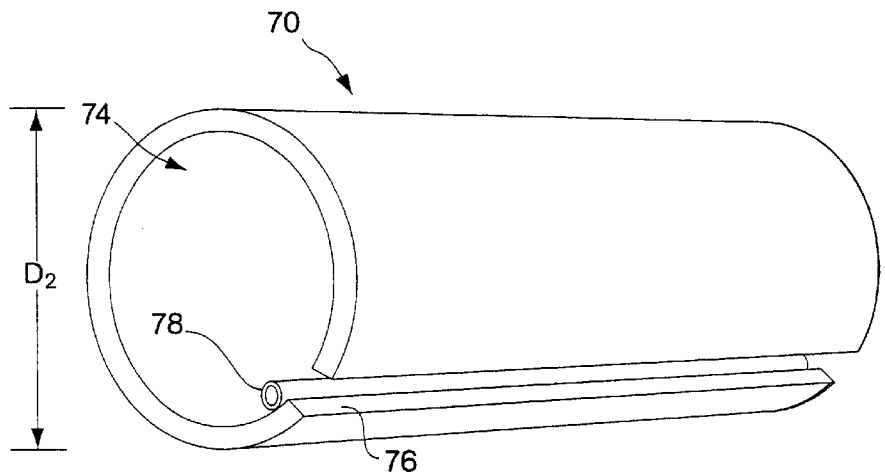
FIG. 7B shows a perspective view of the rolled tube implant in its large profile second configuration.
Figure 8A:
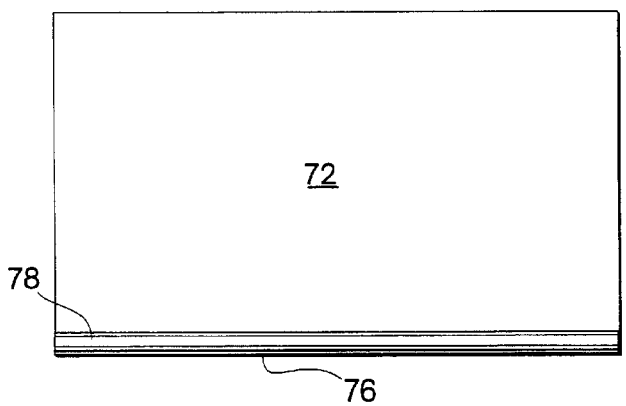
FIG. 8A is a side view of a sheet of material used to form the rolled tube implant.
Figure 8B:
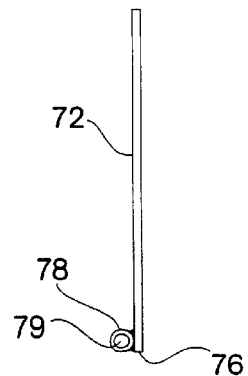
FIG. 8B shows an end view of a sheet of material used to form the rolled tube implant.

FIGS. 7A and 7B show yet another embodiment of the vascular inducing implant comprising a resiliently expandable rolled tube 70. The rolled tube may be fabricated from a flat sheet 72, as shown in FIGS. 8A and 8B. The material is preferably flexible, but will maintain a resilient energy after being bent into a tubular shape tending to maintain the tube in a relatively expanded, large diameter configuration. A metal such as stainless steel or a high density polymer is a preferred material. The tube material may be a solid or may be porous such as a mesh screen. The flat sheet is preferably configured to have formed along one longitudinal edge 76 a tubular ridge 78 that will serve as a lock for holding the sheet in a tubular configuration while being delivered to the tissue location, as will be described in further detail below. The tubular ridge 78 may be a separate tubular segment that is attached to the flat sheet 72 by bonding such as adhesive, soldering or welding. Alternatively the tubular ridge may be formed by curving over a longitudinal edge 72 of the sheet to define a tube along that edge.

Placing the flat sheet into the low profile first configuration requires rolling the flat sheet 72 into a tightly wound roll to define the cylindrical structure of the tubular implant 70. In this first configuration, the rolled tube may be coiled upon itself several times to form a small outer diameter D, as shown in FIG. 7A. Force is required to maintain the rolled tube implant in the first configuration because the elastically deformed sheet material 72 naturally tends to the larger diameter $D_2$ of the second configuration shown in FIG. 7B. The rolled tube is implanted in the tissue in the first configuration shown in FIG. 7A and permitted to expand to its equilibrium configuration represented in FIG. 7B having a larger profile (diameter) than the first configuration.

As with the other embodiments, the expansion of the rolled tube within the subject tissue creates slight injury to the tissue surrounding the implant as well as provides a device for interacting with blood from the surrounding tissue to initiate the process of angiogenesis as was described above. In the case of a rolled-tube formed from a porous or mesh material, further injury to the tissue which surrounds the implant is expected due to the rough surface of the implant material and constant dynamic contact with the tissue. Additionally, the porous or mesh material may enhance fibrin growth through the device to further enhance angiogenesis.

Figure 9A:
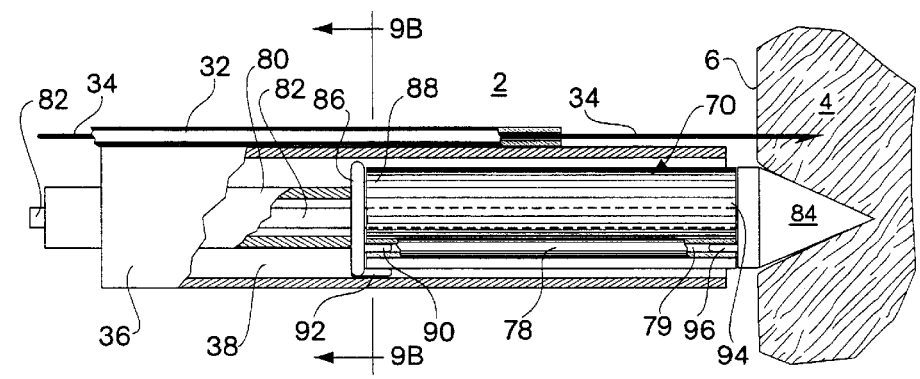
FIG. 9A is a side view and partial cut-away view of the rolled tube implant being delivered to a tissue location through a delivery device.
Figure 9B:
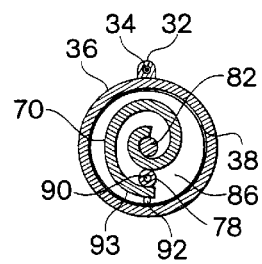
FIG. 9B is a cross-sectional view taken along the line 9A–9B of FIG. 9A.

Delivery of the rolled tube embodiment 70 is shown in FIGS. 9A and 9B. As with the other implant embodiments of the present invention, the rolled tube embodiment may be delivered to the subject tissue percutaneously, thoracically or surgically by a cut-down method. In delivering the implant to myocardial tissue of the heart, percutaneous delivery is preferred because it is least invasive and traumatic to the patient. FIGS. 9A–9D depict delivery of the rolled tube implant percutaneously to the myocardial tissue 4 of the heart. After the left ventricle 2 has been accessed by a steerable delivery catheter 36 as described above, the delivery catheter is anchored in position adjacent the intended tissue location by a barbed tip guidewire 34 that extends through an eccentric guidewire lumen 32 of the delivery catheter. The barbed tip guidewire is anchored in the myocardial tissue 4. The rolled tube 70 is carried through the central lumen 38 of the delivery catheter 36 over a coaxial arrangement of a push tube 80 and piercing wire 82 having a piercing distal tip 84. The piercing wire 82 is longitudinally slidable with respect to the push tube 80 so that it may be extended relative to the push tube to release the rolled tube as will be described below.

The push wire has formed along its length a backstop 86 configured as a disk radially extending from the push tube to provide surface against which the proximal end 88 of the rolled tube can abut during delivery. To restrain the rolled tube in its first configuration during delivery, the backstop may additionally have two longitudinally and distally extending protrusions 90 and 92. The inner protrusion 90 extending within the interior of the tubular ridge 78, which is arranged to be at the edge of the outermost coil 93 of the rolled tube during delivery. The outer protrusion 92 holds the outermost coil 93 from its outer surface, working in conjunction with the inner protrusion to maintain the tube in its small diameter first configuration against the resilient expansive force inherent in the rolled tube. The distal end 94 of the rolled tube is supported in its compact first configuration by a proximally and longitudinally extending protrusion 96 which resides in the interior 79 of the tubular ridge 78 at the distal end 94 of the rolled tube. The protrusion 96 extends proximally from the sharpened distal end 84 of the piercing wire 82.

Figure 9D:
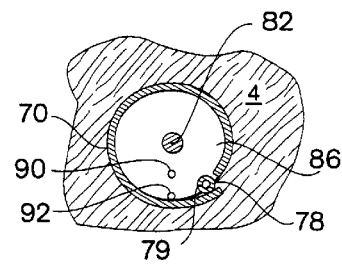
FIG. 9D is a cross-sectional view of the rolled tube implant viewed along the line 9D in FIG. 9C.

With the rolled tube located between the protrusions 90, 92 at the proximal end 88 and piercing wire 82 extending through its interior 74. With the sharpened distal end 84 protruding from the distal end 94 of the rolled tube to pierce the tissue into which it is to be delivered. The protrusion 96 extends proximally, back into the interior 74 of the tube. In this configuration, the push tube, piercing wire and rolled tube combination is advanced, together, distally out of the distal end of the delivery catheter 36 as shown in FIG. 9B so that the piercing distal tip 84 of the piercing wire penetrates the surface of the tissue 6. The assembly is advanced distally into the tissue 4 to a depth that receives the entire implant as shown in FIG. 9D. The proximal end 88 of the implant may, but need not be flush with the surface 6 of the tissue 4.

Figure 9C:
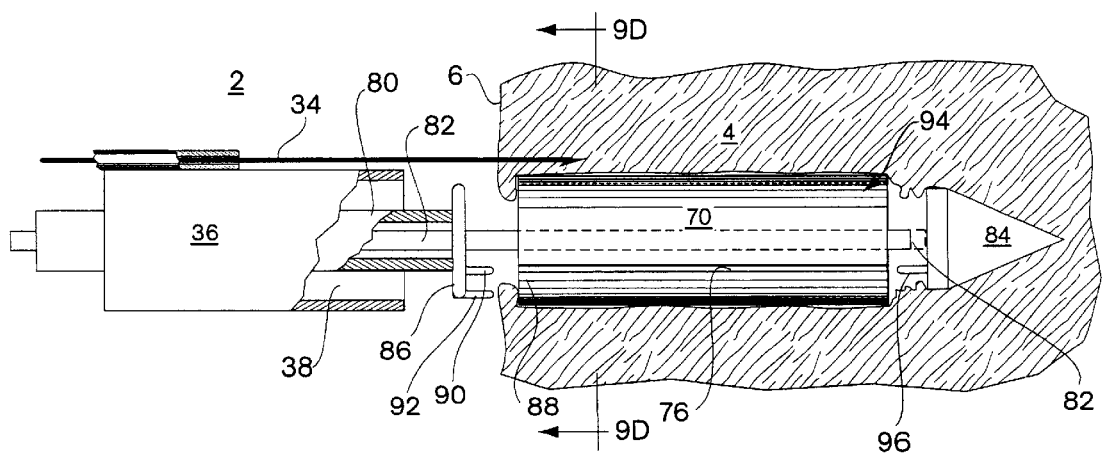
FIG. 9C is a side view illustration of the rolled tube implant placed within tissue and expanded into its second configuration.

After the tube is delivered into the tissue, the piercing wire 82 is moved distally and the push tube 80 is moved proximally, in opposite directions relative to each other, so that the backstop 86 and protrusions 90, 92 and 96 move away from the ends of the tube, releasing it from the confined, first configuration so that it expands to its second, larger profile configuration shown in FIGS. 9C and 9D. After the tube is released from the push tube and piercing wire, the piercing wire is withdrawn proximally through the interior 74 of the now expanded rolled tube 70 into the push tube 80, which is then withdrawn into the delivery catheter 36. The barbed tip guidewire 34 is then pulled from its anchored location within the tissue 4 and the entire delivery catheter 36 is withdrawn from the patient.

Figure 10A:
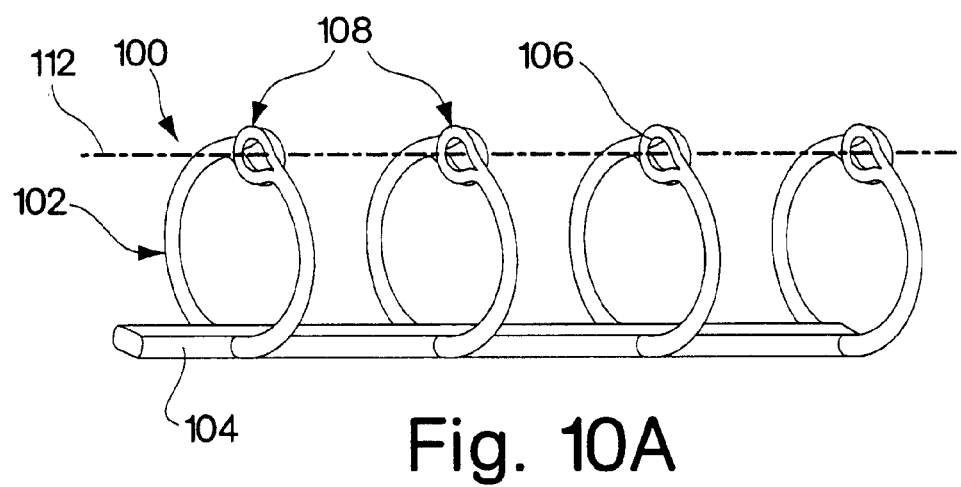
FIG. 10A is a perspective view of an implant comprising a spine and plurality of rings in its small profile first configuration.
Figure 10B:
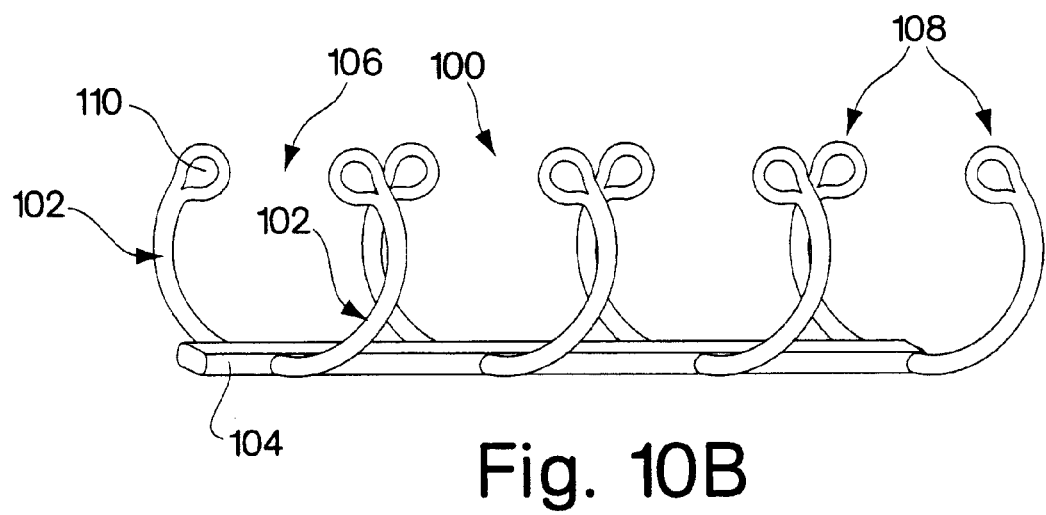
FIG. 10B is a perspective view of the implant comprised of a spine and plurality of rings in its large profile second configuration.

FIG. 10A shows another embodiment of the vascular inducing implants. A spine implant 100 is comprised of a plurality of expandable c-shaped rings 102 concentrically arranged along an axial support or spine 104. Each ring is joined to the spine at a point along their circumference. The spine is tangent to each ring 102, with each ring lying in a plane that is normal to the axis of the spine. A discontinuity 106 at the top of each ring permits the rings to expand between two configurations: a first, low profile configuration in which the ends 108 of the ring overlap to define a ring of relatively small diameter and a second configuration that presents a larger profile, in which the leaves of the ring are open and do not overlap defining a larger diameter and profile.

The spine implant embodiment may be a unitary structure formed from an elastically deformable material such as a plastic or stainless steel. Alternatively, the rings 102 may be separate components that are adjoined to the spine by welding, soldering or bonding. The ends of each ring are preferably formed to have eyelets 110. By locking the eyelets 110 together, the resiliently expandable rings 102 may be maintained in a reduced profile, closed configuration, against the inherent expansive force. An elongate release pin 112, shown in phantom in FIG. 10A, may be inserted through the aligned eyelet pairs of all the closed rings on the spine. The pull pin 112 may be inserted through the eyelets to maintain the rings 102 in a closed configuration by maintaining each ring 102 in a closed configuration, with the eyelets 110 aligned concentrically. The rings 102 may be expanded after implantation within the tissue by pulling the pin from the eyelets to release the rings and permit resilient expansion as will be described in further detail below.

Figure 11A:
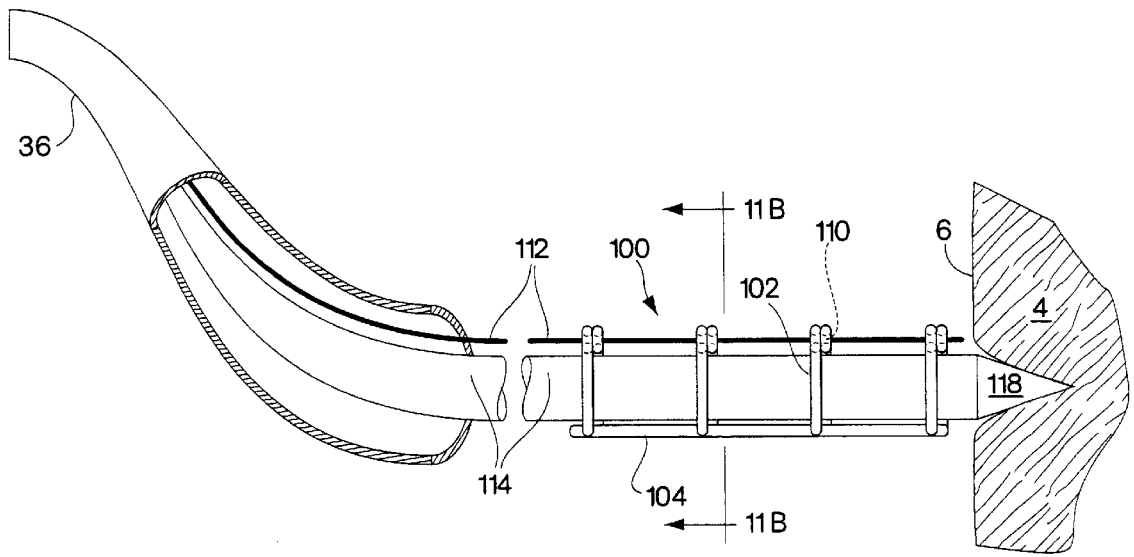
FIG. 11A is a side view of the implant comprised of a spine and plurality of rings in its low profile, first configuration being delivered to a tissue location.
Figure 11C:
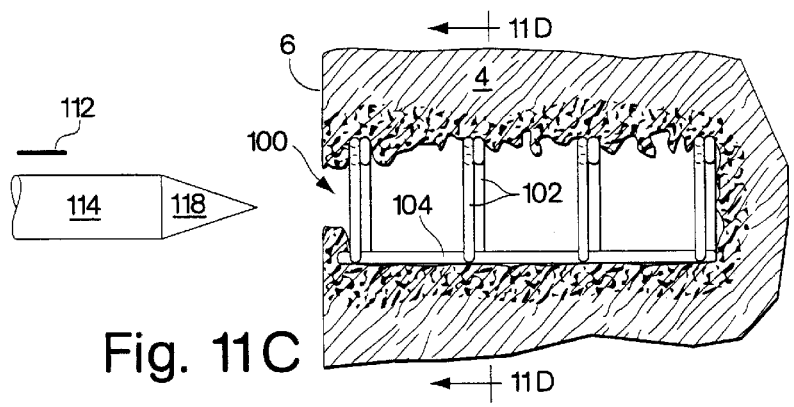
FIG. 11C is a section side view of the implant comprised of a spine and plurality of rings in its large profile, second configuration placed within tissue.
Figure 11B:
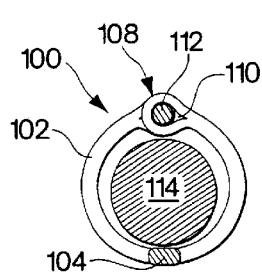
FIG. 11B is a cross-sectional view of the implant comprised of a spine and a plurality of rings viewed along the line 11B—11B in FIG. 11A.

FIGS. 11A–11D illustrate the delivery of the spine implant 100. FIGS. 11A and 11B show the implant in its first, low profile configuration, which is maintained during deliver and insertion into the intended tissue location. As with the other embodiments described above, the implantation of the device will be described as it is implanted into myocardial tissue of the heart. Although the device may be delivered by a variety of methods including surgically or thoracically, the preferred method of delivery is percutaneous, accessing the myocardium 4 through the left ventricle of the heart as is shown in FIGS. 4A–4D.

The spine implant 100 is delivered over a push wire 114 that is slidable through the delivery catheter 36. The push wire extends through the center of the rings during delivery while they are in their closed, small profile configuration. The push wire 114 may be of a diameter which is approximately the same size as the inside diameter of the rings in their closed, small profile configuration to remove any slack between the implant and the push wire during delivery. The pull pin 112 extends through the eyelets 110 and is parallel with the push wire 114 through the delivery catheter 36 where it can be manipulated independently of the push wire at its proximal end extending outside the patient.

Figure 11D:
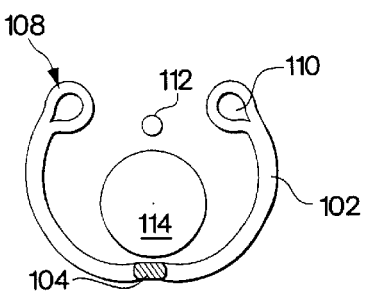
FIG. 11D is a cross-sectional view of the implant comprised of a spine and a plurality of rings viewed along the line 11D—11D in FIG. 11C.

The push wire 114 has a sharpened distal end 118 that is capable of piercing the tissue surface 6 to provide an entry site into which the implant may be inserted into the tissue 4. To prevent proximal movement of the implant on the push wire during delivery into the tissue 4, either the pull pin 112 or the push wire 114 may have formed on its surface a backstop against which the most proximal ring 102 can abut to resist distal movement. After insertion of the implant into the tissue, the pull pin 112 may be pulled proximally to be removed from the eyelets of the rings 110 permitting them to resiliently expand to the open configuration as shown in FIGS. 11C and 11D. After the pull pin has been withdrawn to expand the implant to its second, larger profile configuration, the push wire 114 may be withdrawn proximally through the center of the rings and out of the tissue and the delivery device withdrawn from the patient.

Figure 12A:
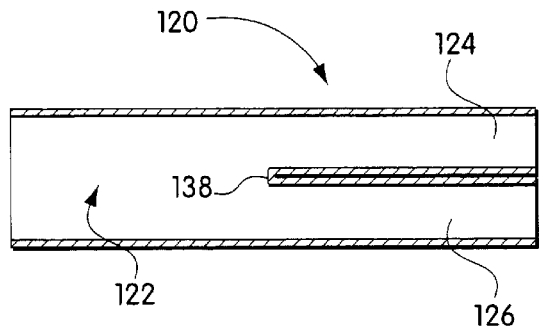
FIG. 12A is a side view of a bifurcated implant in its low profile first configuration.
Figure 12B:
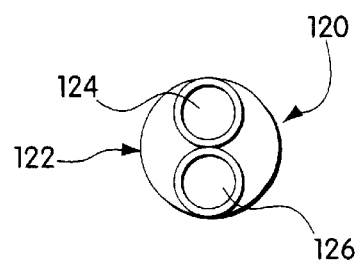
FIG. 12B is a front view of a bifurcated implant in its low profile first configuration.

FIGS. 12A–12D show another embodiment of the implant device having a first configuration that is uniaxial and a second configuration in which a portion of the device becomes biaxial or bifurcated. The bifurcated implant 120 is preferably a hollow unitary structure essentially comprised of three tubular sections arranged similar to a pair of pants. Specifically, the implant has a trunk portion 122 having a generally tubular configuration which splits into a first leg 124 and a second leg 126, each about one-half the diameter of the trunk portion and having a length that is approximately one-half the length of the entire implant. As shown in FIGS. 12A and 12B, the legs 124 and 126 are closed, their longitudinal axes lying parallel to the central axis of the trunk portion 122. In this first configuration, the implant 120 presents a low profile suitable for penetration and delivery into tissue.

Figure 12C:
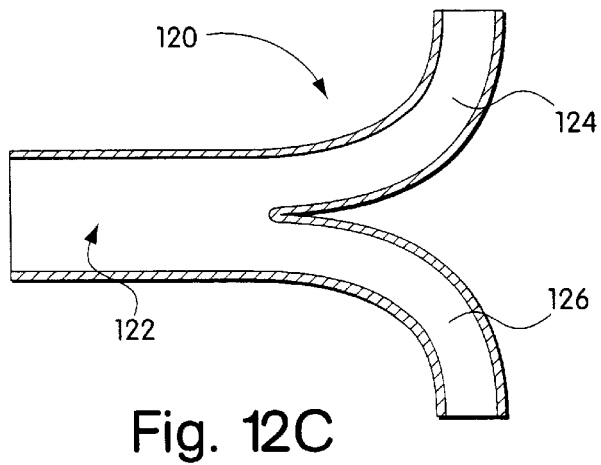
FIG. 12C is a side view of a bifurcated implant in its large profile second configuration.
Figure 12D:
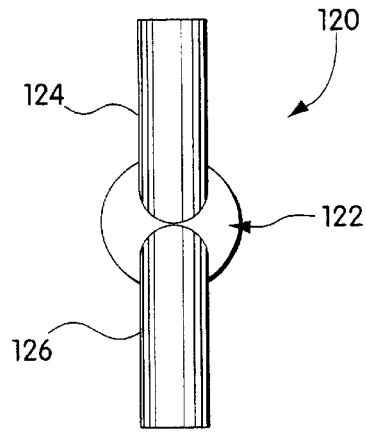
FIG. 12D is a front view of a bifurcated implant in its large profile second configuration.

FIGS. 12C and 12D show the implant in its second, large profile configuration wherein the legs 124 and 126 are split apart; curved away from each other such that their axes approach an angle of 90° relative to the central axis of the trunk portion 122. When moved to the second configuration, the split legs of the implant serve to stress and injure surrounding tissue into which the implant has been inserted. The tearing and abrasion of the tissue surrounding the now expanded legs 124 and 126 respond to the injury through a healing process that leads to angiogenesis as described above. Additionally, because the legs stay in their expanded configuration, the tissue continues to be irritated by the presence of the implant, thereby continuing the injury response and initiation of angiogenesis.

Figure 13:
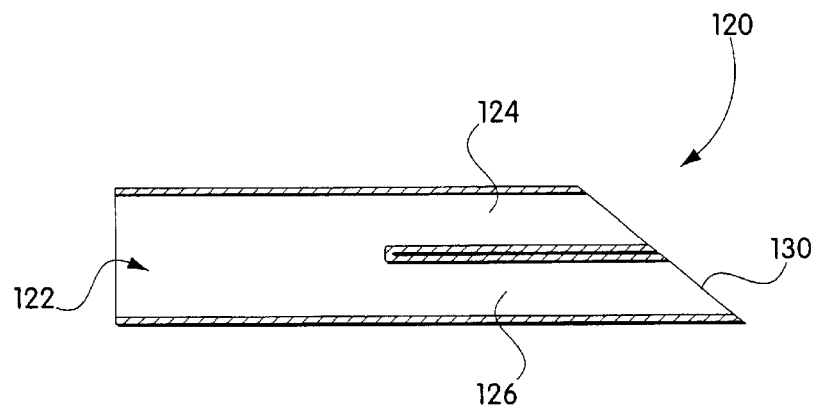
FIG. 13 is a side view of an alternate bifurcated implant having a slanted piercing edge in its low profile first configuration.

FIG. 13 shows a variation of the biaxial implant 120 having a slanted profile edge 130 formed along the ends of the legs 124 and 126 to help to facilitate penetration through the tissue. Although the blunt edge tubular ends of the legs 124 and 126 as shown in FIGS. 12A–12D may be suitable for penetrating soft tissue, the angled edge 130 shown in FIG. 13 provides a sharper profile to pierce tough layers of tissue. The angled edge may be configured in many ways other than the sloping edge shown in FIG. 13. For example, the second leg 126 may have an edge that is angled in the reverse direction from the edge of leg 124 to form an arrowhead profile (not shown).

The biaxial implant may move from its first, compact profile configuration to its second, expanded profile configuration either by inherent resiliency of the implant material, or by a plastic deformation. To expand the plastically deformable embodiment, a splitting force may be applied between the legs of the implant once it has been inserted into tissue. The splitting force may be applied by a pull wire extending through the interior of the implant, having a large profile distal tip that runs between the adjoining legs as the pull wire is moved in a proximal direction and removed from the center of the implant through the trunk portion. Alternatively, and in a preferred method, the implant is resiliently expandable and may be delivered and expanded to the extended tissue location over two guidewires as is described in detail below.

Figure 14A:
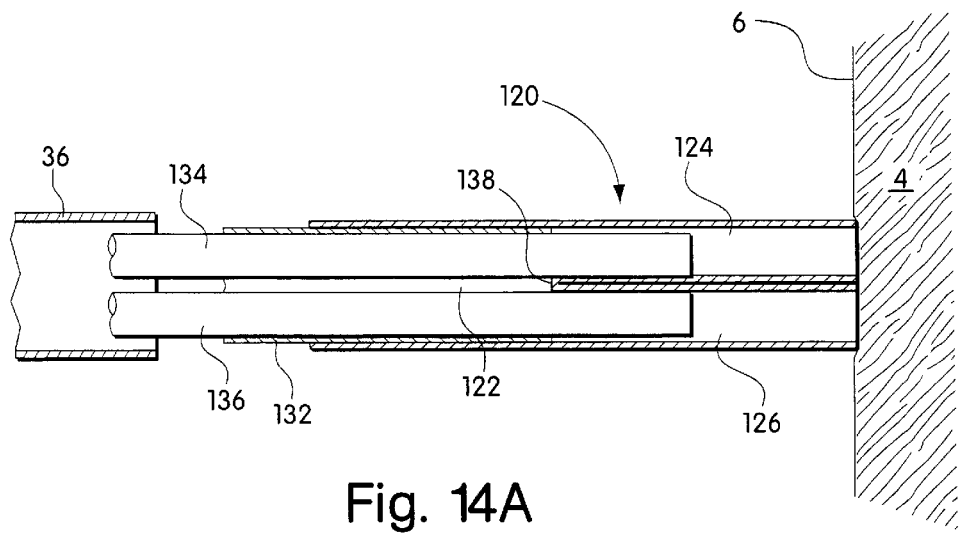
FIG. 14A is a side view of a bifurcated implant in its low profile. first configuration being delivered to a tissue location.
Figure 14B:
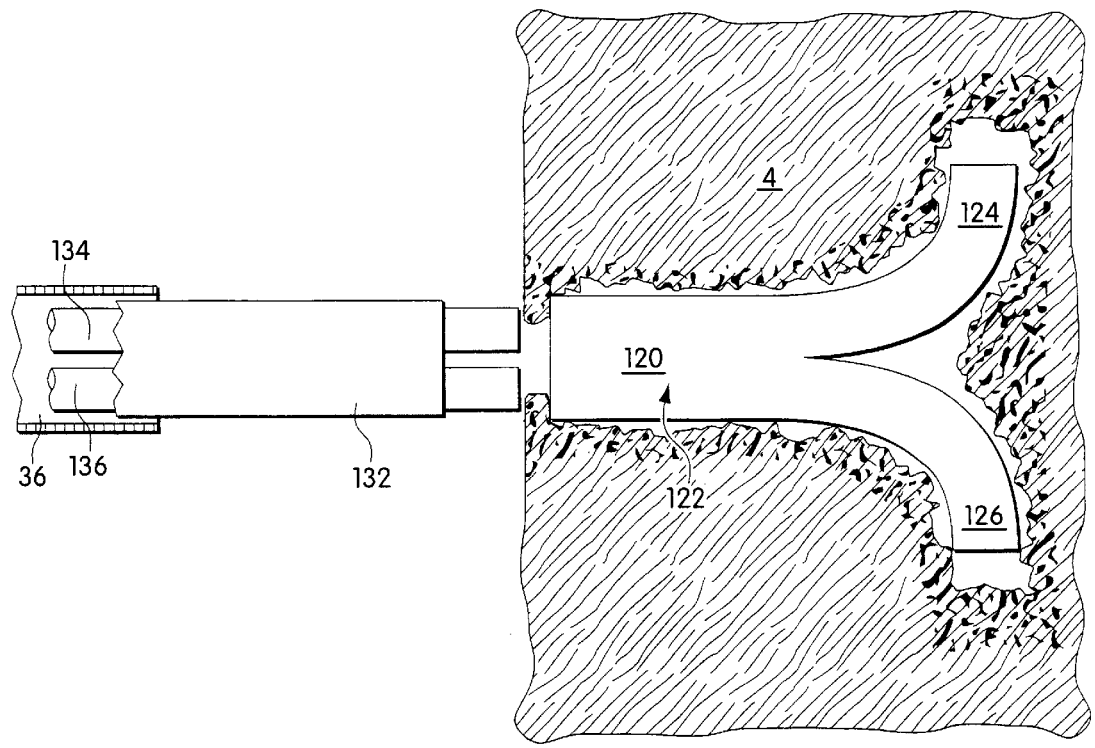
FIG. 14B is a sectional side view of a bifurcated implant in its large profile, second configuration placed within tissue.

FIGS. 14A and 14B illustrate the delivery of the bifurcated implant embodiment into tissue such as myocardial tissue 4 of the myocardium. As was described with relation to the other embodiments, the bifurcated embodiment is preferably delivered percutaneously to the myocardium through a steerable delivery catheter 36 that has been inserted into the left ventricle of the heart adjacent the myocardial tissue to receive the implant. The bifurcated implant 120 is carried through the delivery catheter 36 over a guide tube 132 sized to fit closely the inside diameter of the trunk portion 122 of the implant. Through the guide tube 132 extends two support wires 134 and 136 that extend through the trunk portion of the implant and into the legs 124 and 126 during delivery. The support wires 134, 136 are relatively stiff to maintain the legs 124, 126 in their joined, low profile first configuration as shown in FIG. 14A. The wires and guide tube are slidable relative to each other and through the delivery catheter 36. During delivery, the guide tube extends into the interior of the implant only through the trunk portion 122. The support wires 134, 136 extend distally beyond the trunk portion and into each leg to act as stiffening members, providing axial support from the inside diameter of each leg to resist the resilient force of the legs to bend apart from each other.

During delivery, the entire assembly is moved distally, with the guide tube 132 and wires 134, 136 being pushed distally to expose the implant from the distal end of the delivery catheter 36 so that it may penetrate the endocardial surface 6 and enter the myocardium 4 as shown in FIG. 14B. The delivery force pushing the implant in the distal direction is applied by the distal end of the guide tube 132 engaging the junction of the legs 138. After the implant has been inserted into the tissue 4, the support wires 134 and 136 are withdrawn proximally from the legs 124, 126 of the implant permitting them to expand apart from each other to injure the surrounding tissue and place it in a stressed condition that will be maintained by the implant in its second configuration. In addition to providing a constant source of irritation and injury to the tissue, the expanded implant serves to resist migration out of the tissue despite tissue movement because the implant has clawed into the tissue during expansion. After deployment of the implant the guide tube 132 and support wires 134, 136 are withdrawn further proximally, into the delivery catheter 36, which then may be withdrawn from the patient.

Another embodiment of a bifurcated implant is shown in FIGS. 15A–15D. The open spring bifurcated implant 140 is intended to have a trunk portion 142 and two leg portions 144 and 146 similar to the bifurcated embodiment discussed above. The open spring bifurcated embodiment may comprise two helically wrapped coil springs 148, 150 joined together only at the proximal end 152 of the trunk portion. Alternatively, the bifurcated spring embodiment may comprise a single spring that is wound to double back upon itself at the proximal trunk coil 152 and defining two legs 144 and 146 extending therefrom that are defined by each end of a single spring. The coil spring should be flexible and capable of maintaining substantially its expanded bifurcated and larger profile configuration under the collapsing force of the stressed tissue in which it is implanted.

Figure 15A:
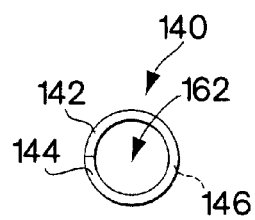
FIG. 15A is a top view of a bifurcated open spring implant in its low profile first configuration.
Figure 15B:
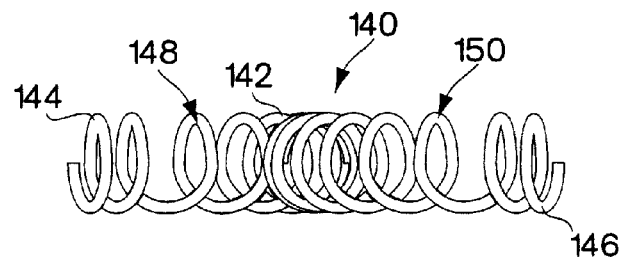
FIG. 15B is a top view of a open spring bifurcated implant in its large profile second configuration.
Figure 15C:
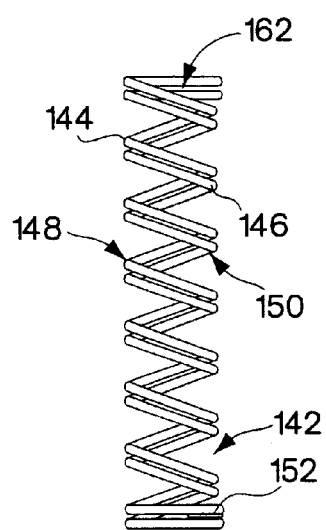
FIG. 15C is a side view of an open spring bifurcated implant in its low profile first configuration.
Figure 15D:
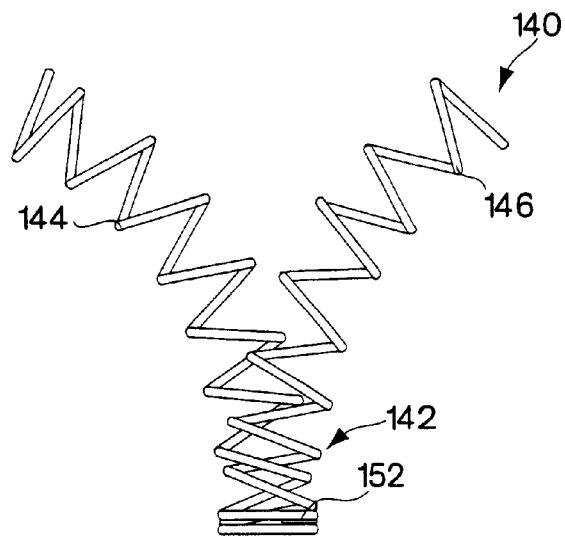
FIG. 15D is a side view of an open spring bifurcated implant in its large profile second configuration.

The first, low profile configuration of the implant is shown in FIGS. 15A and 15C. The coils 152 of each of the legs 144 and 146 interleave so that they substantially lie along the same longitudinal axis as the trunk portion 142. In this configuration, the overall profile of the implant 140 is minimized, facilitating delivery of the implant into tissue. FIGS. 15B and 15D show the implant in its larger profile second configuration. The free ends of each of the legs 144 and 146 spring open, naturally inclined to the Y-shape bifurcated configuration, because they are plastically deformed to have that shape during their formation. The profile of the implant is increased by the movement of the leg portions away from the axis of the trunk portion 142. When permitted to expand within the subject ischemic tissue, the expanding leg portions are expected to cause some minimal injury and possible tearing of the tissue into which it is implanted. The injury, which will be continually irritated by the presence of the implant in its second configuration, is expected to instigate a healing response by the tissue that will initiate angiogenesis by the mechanisms described above.

Figure 16A:
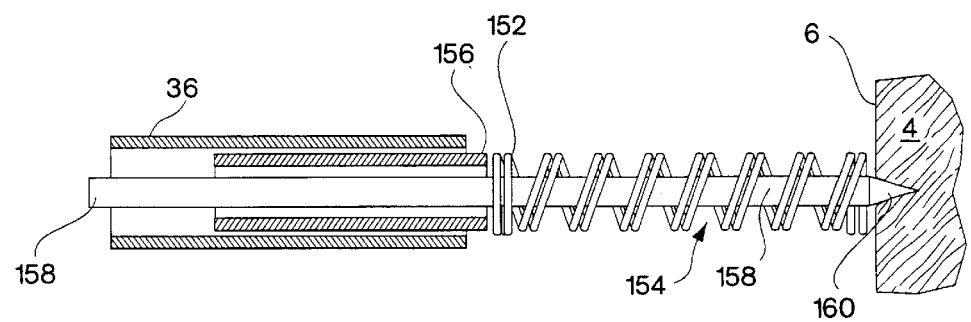
FIG. 16A is a side view of an open spring bifurcated implant being delivered to a tissue location.

FIGS. 16A and 16D illustrate the steps of delivering the bifurcated open spring implant into ischemic tissue 4. In FIG. 16A, the implant is maintained in its uniaxial, low profile first configuration by a relatively stiff piercing wire 158 having a sharpened distal tip 160 for piercing the surface of the tissue 6. The piercing wire 158 extends through the interior 162 of the spring embodiment, retaining the coils 154 of the legs 144 and 146 along the central axis by contacting their inside surfaces. The legs are held against movement by the presence of the wire 158. The sharpened tip 160 of the piercing wire protrudes from the distal end of the implant so that it will be first to contact the tissue during distal movement to the implant site.

Figure 16B:
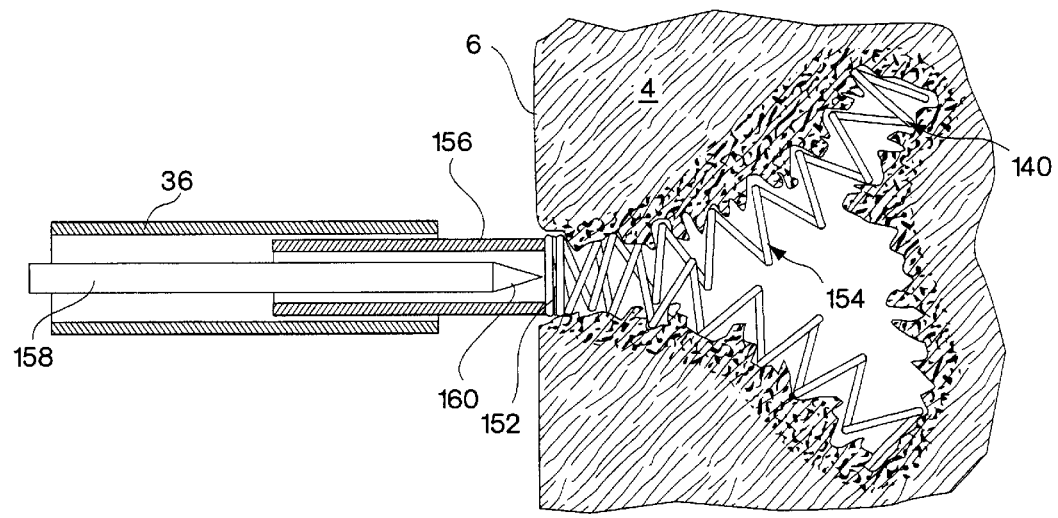
FIG. 16B is a sectional side view of an open spring bifurcated implant located within tissue and expanded to its large profile second configuration.

Push tube 156 is slidable over the push wire and has a larger diameter than the push wire, sized to engage the circumference of the most proximal coil 152 of the implant. The push tube delivers a pushing force against the implant during insertion into the tissue, when both the piercing wire 158 and push tube 156 are moved distally in unison to maintain the piercing wire through the implant which is maintained in its first configuration. Also the push tube 156 can move independently of the piercing wire 158, so that once the implant has been delivered to a proper depth within the tissue 4, the piercing wire 158 may be retracted into the push tube as shown in FIG. 16B, to release the coils 154 to their expanded second configuration. After delivery and release of the implant into the ischemic tissue, the push tube 156 and piercing wire 158 may be retracted proximally into the steerable delivery catheter 36 and the entire assembly withdrawn from the patient.

FIGS. 17A–17D show a variation of the open spring bifurcated implant embodiment. The bifurcated loop implant 170 is comprised of first and second spines 172, 174 each having a plurality of circular loops 176. The loops 176 are joined to the respective spines at a point around their circumference such that they are arranged substantially concentrically. The spines 174, 172 share several common loops 176 in a trunk portion 178 of the implant. The free ends of the spines 172, 174 form leg portions 180, 182 of the implant, respectively. The implant is shown in its first low profile configuration in FIGS. 17A and 17C.

Figure 18A:
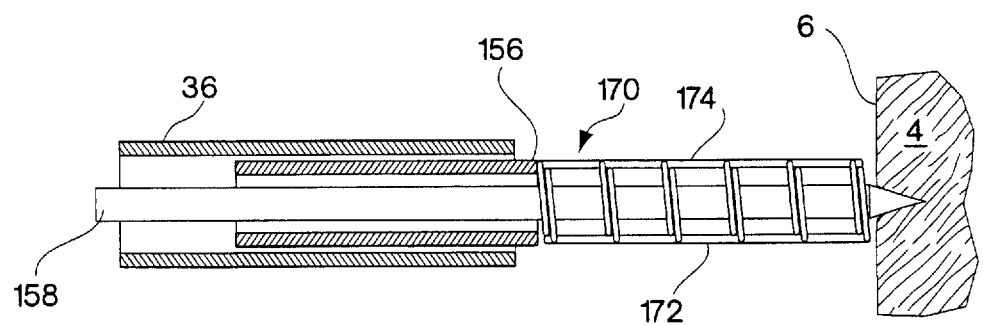
FIG. 18A is a side view of a bifurcated spine and hoop implant in its low profile, first configuration being delivered to a tissue location.
Figure 18B:
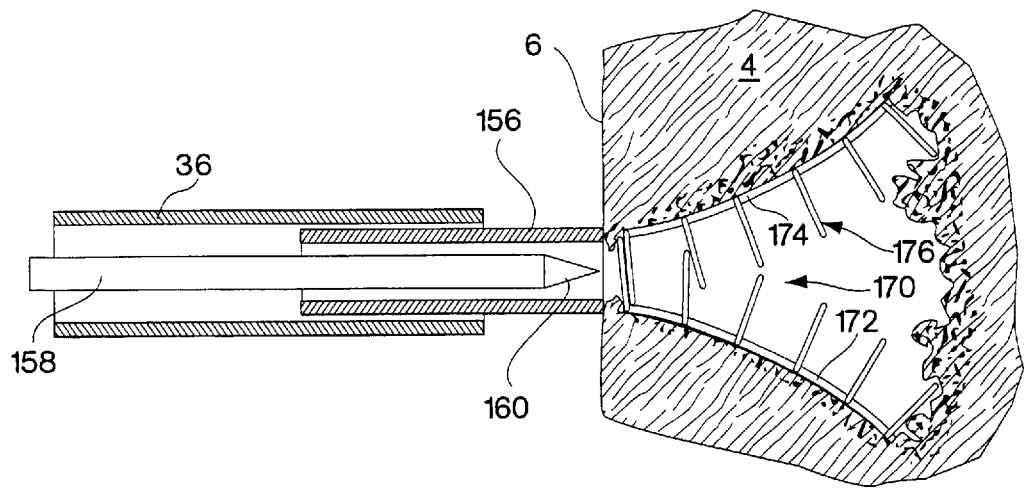
FIG. 18B is a sectional side view of a bifurcated spine and hoop implant placed within tissue and expanded to its large profile second configuration.

In the first configuration, the loops 176 of both spines and the trunk portion are interleaved and lie substantially along the same longitudinal axis. In the expanded second configuration, the leg portions 180 and 182 spring apart under the resilient force of the spines 172 and 174 which are preformed to have a curved configuration, yielding the large profile configuration shown in FIGS. 17B and 17D. The implant is delivered into the subject ischemic tissue 4 by the steps discussed above in connection with the open spring bifurcated embodiment and which are illustrated in FIGS. 18A and 18B. The piercing wire and push tube 158, 156, respectively, may be used to deliver the loop bifurcated implant 170 in the same manner as the open spring embodiment described above.

Another implant embodiment is shown in FIGS. 19A–19D. A brush implant 240 is comprised of a central core member 242 having a plurality of resilient bristles 244 extending radially therefrom to irritate surrounding tissue. The bristles 244 of the brush 240 collapse against the core 242 during distal movement into the tissue during delivery to define a low profile fist configuration. After delivery into the tissue the bristles resiliently expand in a radially outward direction, with respect to the core, to define a larger profile second configuration that irritates and places stress on surrounding tissue.

Figure 19A:
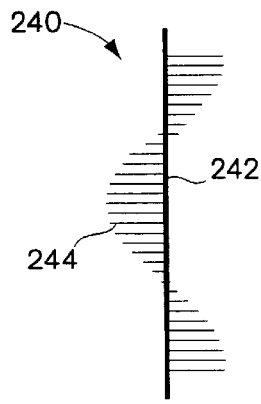
FIG. 19A is a side view of a flexible brush implant.
Figure 19B:
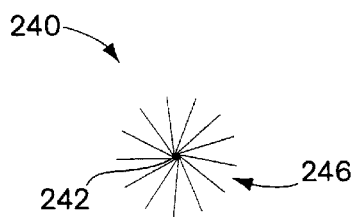
FIG. 19B is an end view of the flexible brush implant.
Figure 19C:
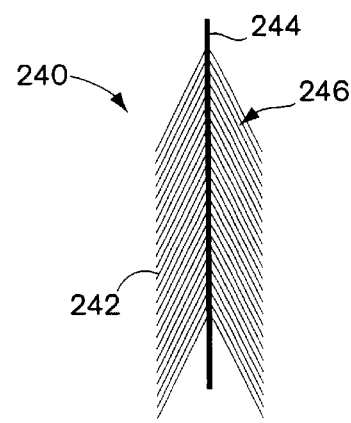
FIG. 19C is a side view of the flexible brush implant at its post delivery configuration.
Figure 19D:
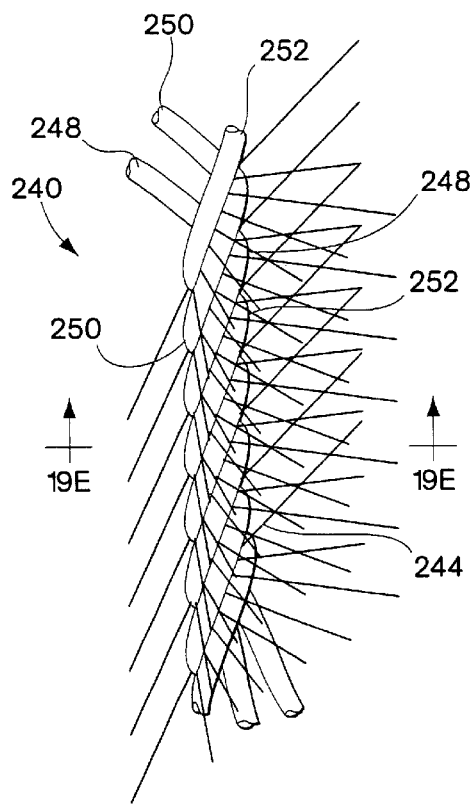
FIG. 19D is a side view of a flexible brush implant having a core formed of twisted wires.
Figure 19E:
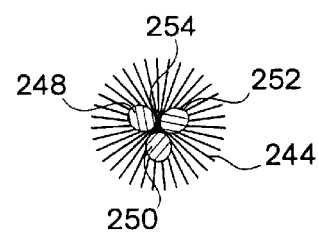
FIG. 19E is a section view of the flexible brush implant show in FIG. 19D.

The central core member 242 is preferably somewhat rigid to facilitate insertion into the tissue 4. The core may be solid or a hollow tube to define a central lumen 246 over which the implant can be delivered into the intended tissue location. Additionally, the central lumen 246 may contain an angiogenic substance to be delivered to the intended tissue location along with the implant. Alternatively, the core 242 of the brush implant may be comprised of several wires helically wrapped around each other along a single axis as shown in FIGS. 19D and 19E. The brush implant shown in FIG. 19D is comprised of three helically wrapped wires 248, 250 and 252 defining the core 242. Wedged in between the wrapped wires are bristles 244 which extend radially from the core 242. As shown in FIG. 19E, the three helically wrapped wires define a central opening 254 through the center of the core. The central opening may be useful for holding an angiogenic substance or thrombus of blood within the implant that will later interact with blood flow after implantation. Additionally, the central opening 254 may receive a guidewire so that the implant may be delivered to its intended location by tracking over the guidewire that has been inserted into a patient. Alternatively, the core 242 may be formed from only two separate wires that are helically wrapped about each other; however, a central opening 254 may not be substantially defined by only two wires.

The bristles 244 attached to the core 242 serve injure and irritate surrounding tissue into which it is implanted to cause an injury response that leads to angiogenesis. The bristles resiliently extend from the core in a radially outward direction to place stress on surrounding tissue and cause irritation. The bristles provide a plurality of contact points with the surrounding tissue where irritation occurs, providing a plurality of nucleation sites where angiogenesis can be initiated.

Tubes may be used in place of the wires that form the core 242 and also the bristles 244. Tubular bristles and core wires provide lumens that can retain a quantity of an angiogenic substance or thrombi of blood intended to interact with the surrounding tissue into which the device is implanted. The core wires may have an outside diameter of 0.008 inch and the bristles may have an outside diameter on the order of 0.006 inch to 0.010 inch. The bristles may be made from stainless steel or plastic.

Figure 19F:
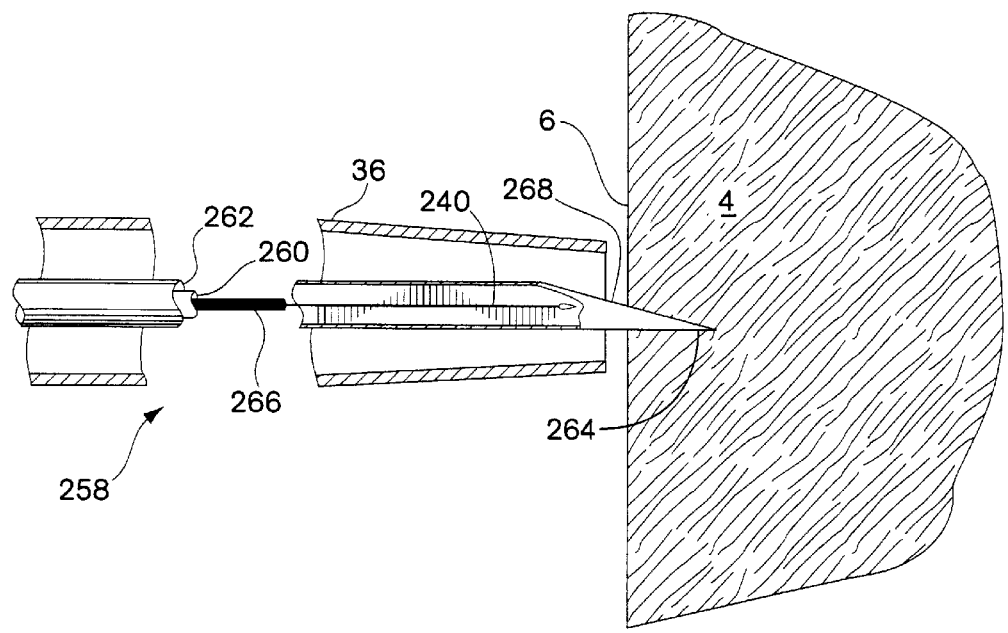
FIG. 19F is a partial cut-away view of the flexible brush implant and associated delivery system penetrating the intended tissue location.

As with the embodiments described above, the brush implant may be delivered percutaneously, thoracically or surgically via a cut-down method to the intended tissue location. By way of example, FIG. 19F represents the brush implant being delivered percutaneously into the myocardium 4. A suitable delivery system for the brush type implant may include a steerable outer catheter 36 within which a slidable smaller diameter brush carrier catheter 260 having a central lumen 262. The distal end 264 of the brush carrier catheter is sharpened to be capable of piercing the endocardial surface of the myocardium 8.

Figure 19G:
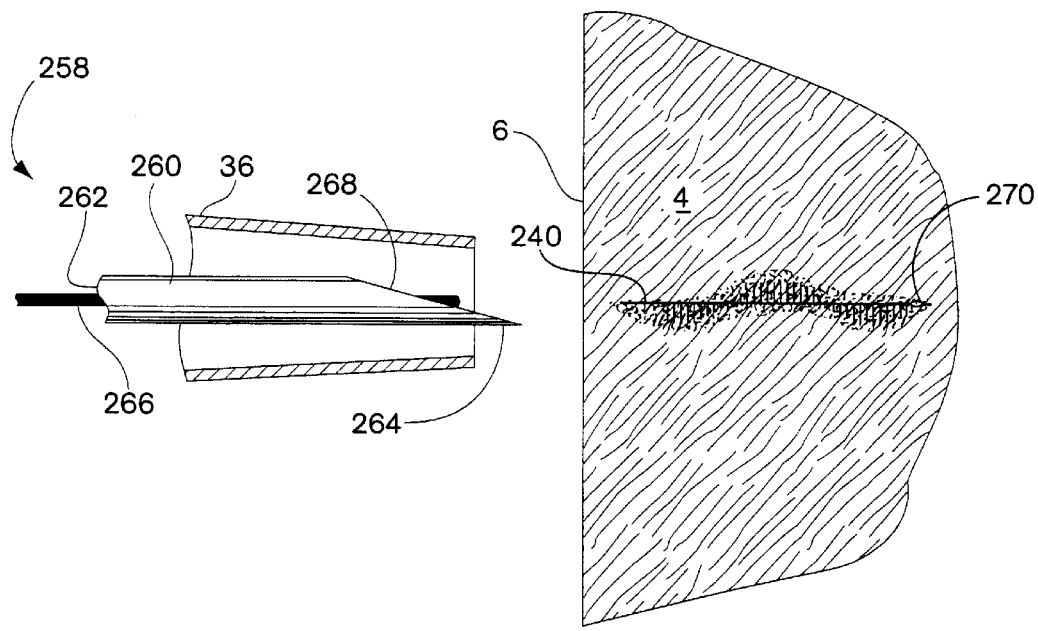
FIG. 19G is a partial cut-away view of an implanted flexible brush implant and its associated delivery system being withdrawn.

A brush implant 240 is pushed through the central lumen 262 of the catheter 260 in a distal direction by a push wire 266 that is also sized to fit within a central lumen of the catheter. Therefore, to deliver a brush implant into tissue, the distal end of the steerable catheter 36 is brought in proximity to the intended tissue location as shown in FIGS. 19F and 19G. The brush carrier catheter carrying a brush implant 240 and push wire 266 within its central lumen 262 is navigated distally through the steerable catheter and out its distal end so that the sharpened distal end 264 of the catheter will pierce the surface of the tissue to permit delivery of the implant. After the distal end of the catheter has been advanced slightly into the tissue 4, the push wire 266 is moved distally to push the brush implant 240 out of the distal opening 268 of the catheter 260.

Alternatively, the distal end of the brush carrier catheter 264 need not be sharpened to pierce the tissue implant location. Rather, the brush implant itself may have a sharpened distal tip 270 formed by the wrapped wires or hypotube of the core 242 that is capable of penetrating the tissue 4 with pushing force provided from the push wire 266. After implantation, the push wire 266 and brush carrier catheter 266 may be withdrawn proximally back into the steerable catheter 36 and the implant system 258 withdrawn from the patient. The distal movement through the tissue that occurs during implantation causes the bristles 244 to maintain an acute angle with a longitudinal axis of the brush implant, pointing in the proximal direction. After the brush is implanted, the bristles tend to resiliently return to a radially outward extending position that places stress on the surrounding tissue and causes irritation. Additionally, the bristles act as barbs to prevent proximal migration of the implant.

From the foregoing it will be appreciated that the invention provides an implant and delivery system for promoting angiogenesis within ischemic, viable tissue. The invention is particularly advantageous in promoting angiogenesis with an ischemic myocardial tissue of the heart. The implants are simple and readily insertable into the intended tissue location with a minimum of steps. The delivery systems are simple to operate to implant the devices quickly and safely.

It should be understood, however, that the foregoing description of the invention is intended to be illustrative thereof and that other modifications, embodiments and equivalents may be apparent to those skilled in the art without departing from its spirit.

Having thus described the invention what we desire to claim and secure by Letters Patent is:

1. A tissue implant device for implantation into ischemic tissue comprising:
   an implant having a first configuration with a first profile and a second configuration having a second profile that is greater than the first profile whereby surrounding tissue into which the implant is placed in stress and is irritated sufficiently to cause an injury response including thrombosis formation that initiates angiogenesis;
   the implant comprising a plurality of expandable members each having a free end and an end joined to the implant, each member configured to diverge away from a substantially common central longitudinal axis of the implant during self-expansion from the first configuration to the second configuration.

2. An implant as defined in claim 1 further comprising a spring that is resiliently expandable from the first configuration to the second configuration.

3. An implant device as defined in claim 1 wherein the implant defines a hollow interior.

4. An implant device as defined in claim 1 wherein the implant is flexible after assuming the second configuration.

5. An implant device as defined in claim 1 wherein the implant is bifurcated defining a trunk portion aligned along the longitudinal axis of the implant and defining expandable members that are legs extending from the trunk portion and that diverge away from the longitudinal axis upon expansion.

6. An implant device as defined in claim 1 wherein a first portion of the body aligned along the longitudinal axis of the implant remains static during and after delivery and a second portion of the body is defined by expandable members that move to a different position relative to the first portion after implantation to comprise a second configuration of the device.

7. An implant device as defined in claim 6 wherein the implant comprises an elastic material and the motivational energy to cause the implant to move from the first to the second configuration is the inherent resiliency of the material.

8. An implant device as defined in claim 7 wherein the first portion is a cylinder and the second portion is defined by at least one cylinder, smaller than the cylinder of the first portion, extending from and attached to the first portion at one end, and a second end being free.

9. An implant device as defined in claim 8 wherein the free end of the second portion is configured to pierce the tissue.

10. An implant device as defined in claim 1 wherein a portion of the body lying along the longitudinal axis is defined by an axial member and the expandable members are defined by a plurality of C-shaped rings joined to the axial member and lying within a plane that is substantially perpendicular to the axial member.

11. An implant device as defined in claim 2 wherein the body is comprised of a tube rolled from a flat sheet.

12. An implant as defined in claim 1 wherein the implant comprises a brush comprising a core that lines along the longitudinal axis and expandable members that comprise a plurality of resilient bristles extending from the core at a first angle, acute to the core, in its low profile first configuration and extending from the core at an angle greater than the first angle in its large profile second configuration.

13. An implant as defined in claim 12 wherein the core defines an interior.

14. An implant as defined in claim 12 wherein the bristles are tubular, each defining an interior.

15. An implant as defined in claim 12 wherein the bristles are configured to carry an angiogenic substance.

* * * * *